US009155833B2

(12) United States Patent
Nelson et al.

(10) Patent No.: US 9,155,833 B2
(45) Date of Patent: Oct. 13, 2015

(54) SYSTEMS AND METHODS FOR MONITORING THE USE OF MEDICATIONS

(75) Inventors: Elizabeth Nelson, Newton, MA (US); David Feygin, Glen Rock, NJ (US); Richard Byrd, Glen Rock, NJ (US); Bart D. Peterson, Farmington, UT (US); Karthik Ranganathan, Edgewater, NJ (US); Weston F. Harding, Lehi, UT (US); Ralph L. Sonderegger, Farmington, UT (US); William R. Marshall, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 833 days.

(21) Appl. No.: 13/410,067

(22) Filed: Mar. 1, 2012

(65) Prior Publication Data
US 2012/0226446 A1    Sep. 6, 2012

Related U.S. Application Data

(60) Provisional application No. 61/449,263, filed on Mar. 4, 2011, provisional application No. 61/449,314, filed on Mar. 4, 2011, provisional application No. 61/450,204, filed on Mar. 8, 2011, provisional application No. 61/450,198, filed on Mar. 8, 2011.

(51) Int. Cl.
*G01N 31/00* (2006.01)
*A61M 5/168* (2006.01)
*G06F 19/00* (2011.01)

(52) U.S. Cl.
CPC .............. *A61M 5/168* (2013.01); *G06F 19/34* (2013.01); *G06F 19/3468* (2013.01)

(58) Field of Classification Search
CPC .... A61B 5/0006; A61B 5/0008; A61B 5/002; A61B 5/0022; A61B 5/02055; A61B 5/0402; A61B 5/0488; G06F 19/3418; G06F 19/345; G06F 19/3462; G06F 19/3406; G06F 19/3456; G01N 2035/00673
See application file for complete search history.

(56) References Cited

U.S. PATENT DOCUMENTS

| 3,631,437 | A | | 12/1971 | Campbell |
| 4,607,671 | A | | 8/1986 | Aalto et al. |
| 4,759,756 | A | | 7/1988 | Forman et al. |
| 4,846,005 | A | | 7/1989 | Bacehowski et al. |
| 5,046,496 | A | | 9/1991 | Betts et al. |
| 5,145,565 | A | | 9/1992 | Kater et al. |
| 5,301,543 | A | * | 4/1994 | Reichert ............... 73/64.45 |
| 5,390,671 | A | | 2/1995 | Lord et al. |
| 5,563,584 | A | | 10/1996 | Rader et al. |
| 5,620,008 | A | | 4/1997 | Shinar et al. |

(Continued)

FOREIGN PATENT DOCUMENTS

EP    1 739 585 A2    1/2007
WO    WO 02/096781 A1    12/2002

(Continued)

*Primary Examiner* — Elias Desta
(74) *Attorney, Agent, or Firm* — Jeanne Lukasavage; Craig Metcalf; Kirton McConkie

(57) ABSTRACT

Systems and methods for monitoring the use of a fluid over the lifecycle of the fluid, said systems including a plurality of fluid identification stations, each station having one or more sensors to detect and identify a parameter of a fluid, wherein a each station is operably interconnected thereby permitting each station to access and verify the identity of a fluid as determined by each independent fluid identification station.

18 Claims, 20 Drawing Sheets

(56) References Cited

U.S. PATENT DOCUMENTS

| | | | |
|---|---|---|---|
| 6,193,675 B1 | 2/2001 | Kraus et al. | |
| 6,264,611 B1 | 7/2001 | Ishikawa et al. | |
| 6,753,186 B2 * | 6/2004 | Moskoff | 436/125 |
| 6,758,835 B2 | 7/2004 | Close et al. | |
| 7,533,028 B2 | 5/2009 | Mallett et al. | |
| 7,811,279 B2 | 10/2010 | John | |
| 8,287,073 B2 * | 10/2012 | Schippers | 347/14 |
| 2003/0100861 A1 | 5/2003 | Bergeron et al. | |
| 2004/0171983 A1 | 9/2004 | Sparks et al. | |
| 2006/0253297 A1 | 11/2006 | Mallett et al. | |
| 2007/0100518 A1 | 5/2007 | Cooper | |
| 2007/0135779 A1 | 6/2007 | Lalomia et al. | |
| 2007/0179448 A1 | 8/2007 | Lim et al. | |
| 2007/0191700 A1 | 8/2007 | Say et al. | |
| 2008/0129475 A1 | 6/2008 | Breed et al. | |
| 2008/0169044 A1 * | 7/2008 | Osborne et al. | 141/1 |
| 2008/0237092 A1 | 10/2008 | Mallett et al. | |
| 2008/0319795 A1 | 12/2008 | Poteet et al. | |
| 2009/0036764 A1 | 2/2009 | Rivas et al. | |
| 2009/0216205 A1 | 8/2009 | Ryan et al. | |
| 2009/0275815 A1 | 11/2009 | Bickoff et al. | |
| 2010/0145274 A1 | 6/2010 | Royce | |
| 2010/0191084 A1 | 7/2010 | Shah et al. | |
| 2010/0280486 A1 | 11/2010 | Khair et al. | |
| 2010/0305499 A1 | 12/2010 | Matsiev et al. | |
| 2011/0009817 A1 | 1/2011 | Bennett et al. | |
| 2011/0015583 A1 | 1/2011 | Davis et al. | |
| 2011/0060198 A1 | 3/2011 | Bennett et al. | |
| 2011/0060229 A1 | 3/2011 | Hulvershorn et al. | |
| 2011/0112474 A1 | 5/2011 | Bochenko et al. | |
| 2011/0144530 A1 | 6/2011 | Felder | |
| 2011/0264069 A1 | 10/2011 | Bochenko | |
| 2011/0270027 A1 | 11/2011 | Augarten et al. | |
| 2012/0016345 A1 | 1/2012 | Carter et al. | |
| 2012/0065617 A1 | 3/2012 | Matsiev et al. | |
| 2013/0177455 A1 | 7/2013 | Kamen et al. | |
| 2013/0226137 A1 | 8/2013 | Brown | |

FOREIGN PATENT DOCUMENTS

| | | |
|---|---|---|
| WO | WO 2004/033003 A1 | 4/2004 |
| WO | WO 2004/095379 A1 | 11/2004 |
| WO | WO 2009/114115 A1 | 9/2009 |

* cited by examiner

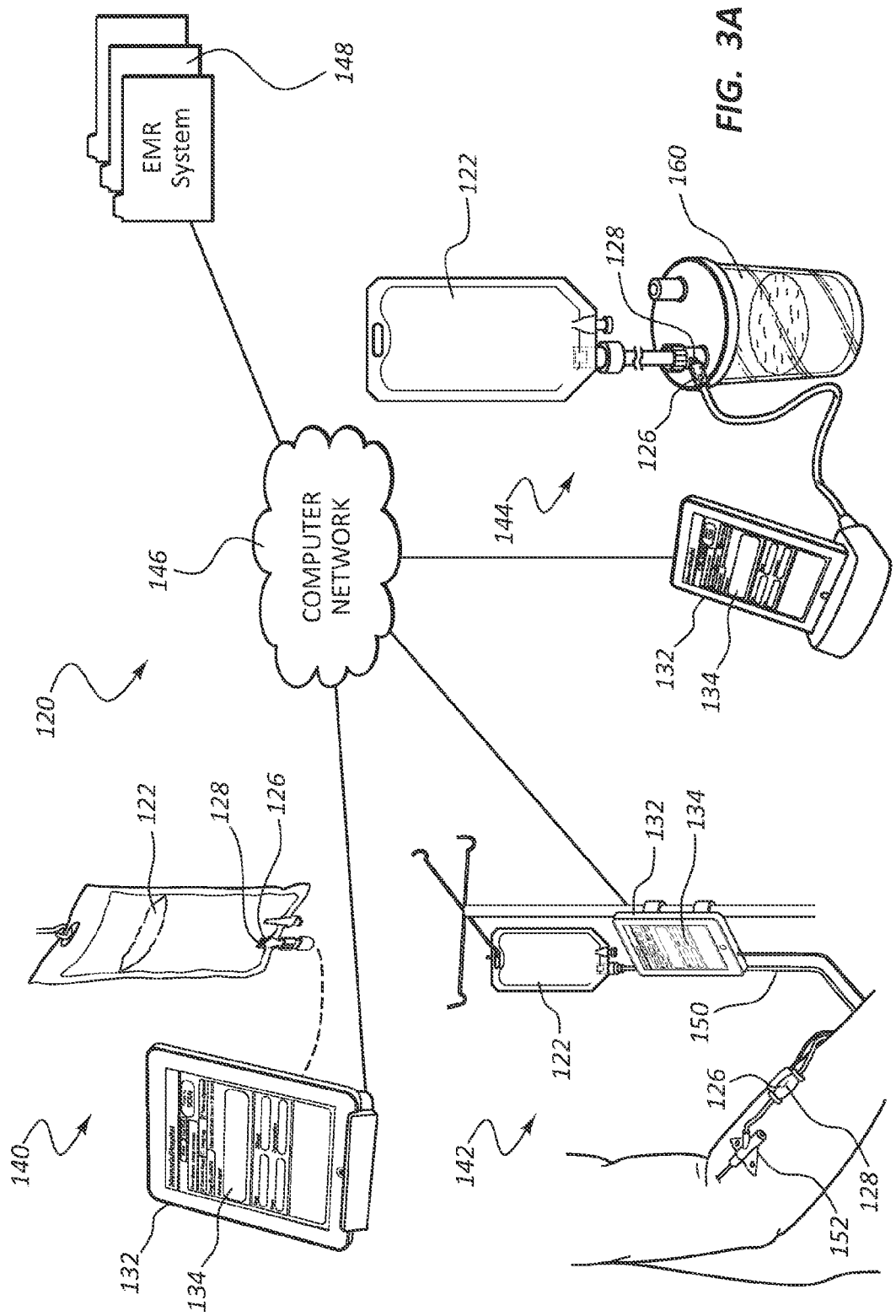

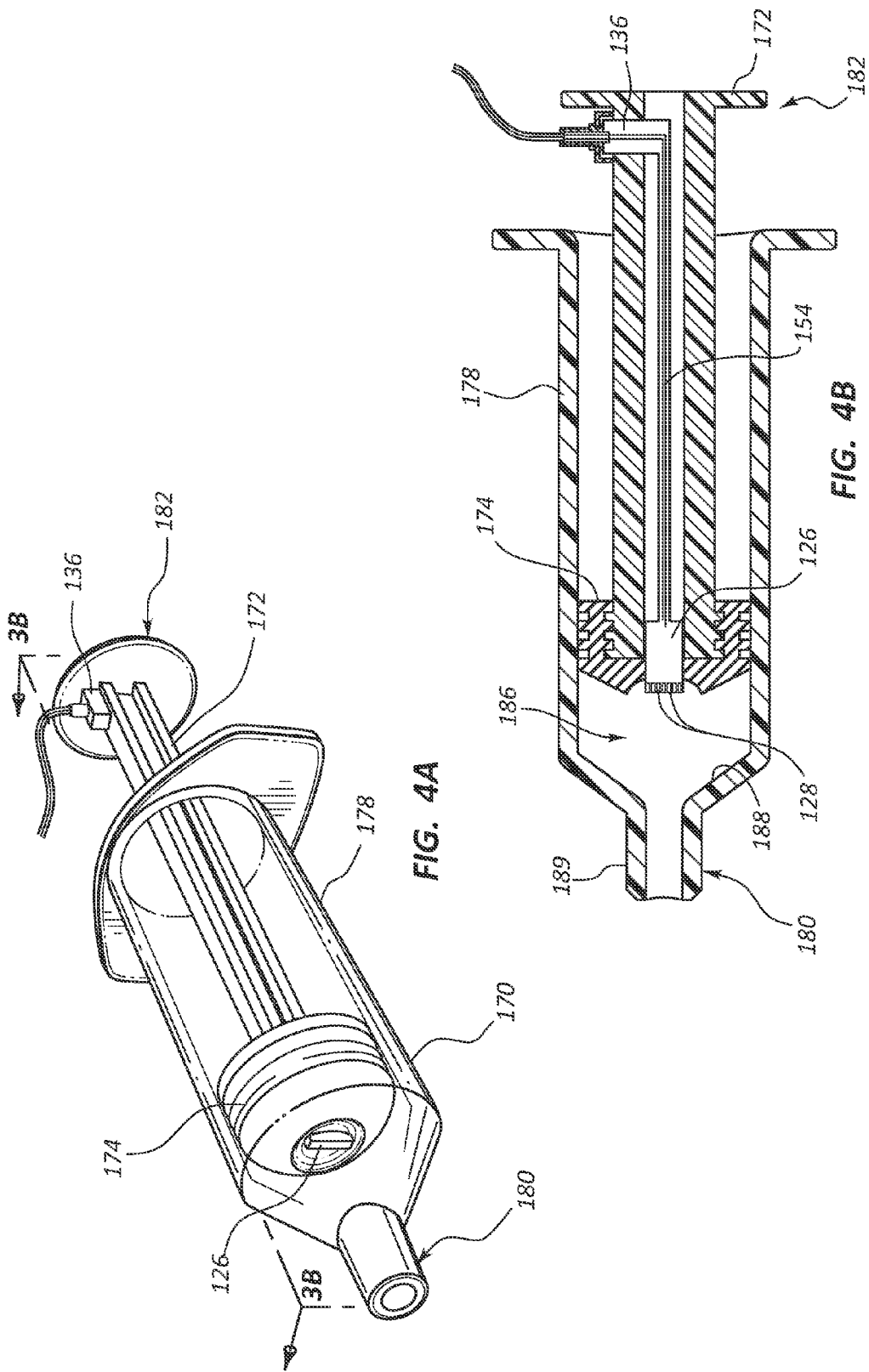

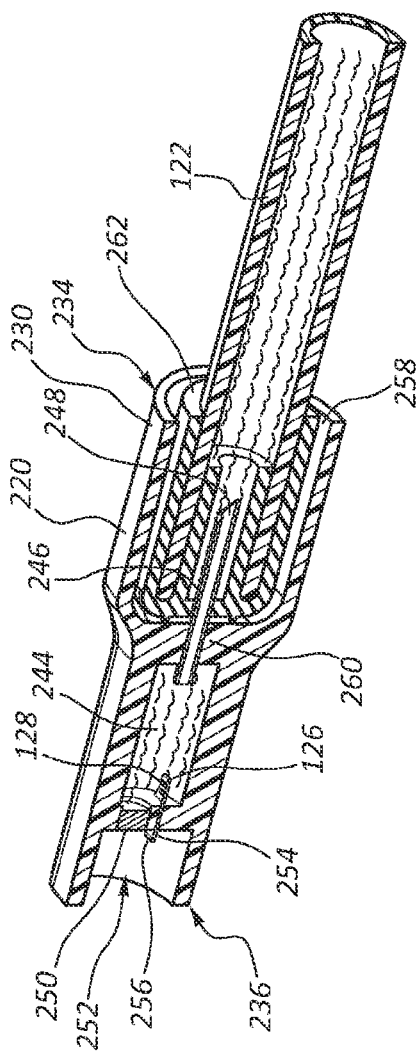
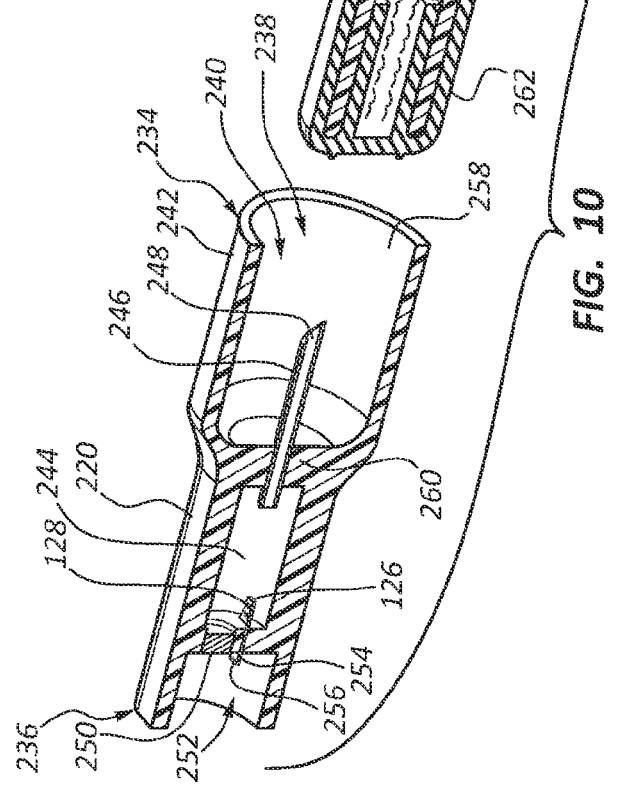
FIG. 11
FIG. 10

SYSTEMS AND METHODS FOR MONITORING THE USE OF MEDICATIONS

RELATED APPLICATIONS

This application claims the benefit of U.S. Provisional Application No. 61/449,263 filed Mar. 4, 2011, entitled SMART CLOSED LOOP MEDICATION ADMINISTRATION, U.S. Provisional Patent Application No. 61/449,314 filed Mar. 4, 2011, entitled SMART DELIVERY CONTAINER, U.S. Provisional Application No. 61/450,204 filed Mar. 8, 2011, entitled SMART DRUG CONTAINER ATTACHMENT, and U.S. Provisional Application No. 61/450,198 filed Mar. 8, 2011, entitled SMART WASTE DISPOSAL, each of which is incorporated herein by reference in their entirety.

BACKGROUND

Hospitals and other care facilities face many challenges surrounding the preparation, use, and wasting of injectable drugs. For instance each year many preventable adverse drug events involving harmful medication errors are caused by injectable drugs. Acute care facilities, such as hospitals, emergency departments, patient cancer clinics, urgent care centers, and some long-term-care hospitals and facilities, account for many of these adverse drug events. Most injectable medication errors occur at the administration stage. These errors include, for instance, administering the incorrect drug (which can be cause by improperly labeling a drug or administering the drug to the wrong patient), administering the incorrect drug dose, administering a drug having an incorrect drug concentration (this can include a fluid having a drug that has not been mixed properly), administering an expired or contaminated drug, incorrectly administering a second dose of a drug, administering the drug at the wrong rate, and administering a drug at a wrong time. Such medication errors are particularly challenging because they can be difficult or impossible for some care facilities to detect.

Another challenge presented to care facilities is a growing concern of drug diversions and drug abuse within these facilities. Recent reports have stated that the use of narcotics within the hospital is becoming an increasing problem. In an effort to avoid drug diversions, some hospitals and other care facilities have protocols in place that require one person to dispose or waste the narcotic (such as into a sink or a container) while another person watches to ensure the narcotic was indeed wasted. There are inherent problems with this method. For example, the drug could be substituted prior to wasting without the observer knowing, the waster and observer could be diverting the drug together, or the observer ignores the problem for professional or personal reasons.

In light of the high rate of harmful medication errors, drug diversions, and drug abuse that occur despite current practices and technologies, it would be beneficial to develop systems and methods that can be used by care facilities to further reduce the occurrence of these adverse events.

BRIEF SUMMARY OF THE INVENTION

The present invention has been developed in response to problems and needs in the art that have not yet been fully resolved by currently available vascular access systems and methods. Thus, these systems and methods are developed to monitor the use of any fluid. For example, these systems and methods are developed to monitor the use of any injectable fluid, any intravenous (IV) fluids, and/or any liquid oral medications (herein referred to simply as a fluid or an IV fluid). The present systems and methods can provide a closed-loop medication monitoring system that identifies and records the preparation, use, wasting, or re-dispensing of medications. These systems and methods can be useful to scientifically verify the contents of fluids containing one or more drugs at various stages, to record the use of IV fluids for inventory management and patient billing purposes, and for ensuring that the IV fluids are administered properly to patients.

These systems and methods utilize several sensor systems. Each sensor system can include a sensor and a processor unit. The sensor can be configured to contact a fluid and perform one or more tests on the fluid. The processor unit receives a sensor measurement from the sensor and uses those measurements to identify one or more of the contents and characteristics of the fluid. This can be referred to as identifying the fluid. The contents and characteristics of the fluid can include the identity of one or more drugs within the fluid, the concentration or dose of the one or more drugs, any degradation (e.g., expiration or contamination) of the one or more drugs, the temperature of the fluid, and the volume of the fluid. Each of these sensor systems can be utilized at different locations within a care facility and/or be used at different stages of the lifecycle of a fluid.

For instance, a first fluid identification system can be used to ensure that the fluid is properly prepared. After a fluid is prepared, it can be placed in a container such as a syringe or an IV bag. To verify that the fluid was properly prepared, a first fluid identification system can be coupled to the container such that a sensor of the first fluid identification system is in fluidic contact with the fluid inside the container. When activated, the sensor identifies and verifies the fluid within the container before it is administered to a patient. In some instances, a medication or fluid is matched to the patient record before activation. Accordingly, where the fluid does not match the patient record, administration of the fluid is prevented.

The sensor of the first fluid identification system may be embedded within the container or included in a removable attachment device. Once the fluid is identified, this identification can be stored on a computer network, including for instance an electronic medical record (EMR) system or other such data tracking system. The identification of the fluid may further be recorded along with other relevant information, such as the initial volume of the fluid, time of administration, an identification of the container, the name of the pharmacist who prepared the fluid, and the drug lot number for manufacture.

In some instances, a second fluid identification system is used to monitor the administration of a fluid into a patient. This identification system generally includes a sensor that is connected to an IV administration system or other device such that it can identify fluid flowing to the patient. For example, in some implementations the second fluid identification system includes a sensor capable of identifying one or more drugs flowing into the patient, the dose for concentration of the drugs, flow rate of the fluid, the volume of fluid administered to the patient, and/or the temperature of the fluid. This second fluid identification system may further be used to detect medication errors and other problems that occur during IV administration and to alert a caregiver or clinician regarding potential problems or errors. The identification system can also record the identity of the fluid, such as on an EMR system.

In some instances, a third fluid identification system is used to monitor the wasting of a fluid into a waste disposal unit, such as a waste container or a drain. This third system may further include a sensor that is connected to the waste disposal unit such that the sensor is capable of identifying the fluid being wasted. In some instances, the sensor of the third fluid identification system is capable of identifying the volume of the wasted fluid along with the identity of one or more drugs within the fluid and the concentration of such drugs. This third identification system may further have access to information provided by the first and second fluid identification systems to assist the third identification system in determining whether a fluid has been diverted, illegally modified, or stolen.

In some implementations of the present invention, one or more of fluid identification systems is incorporated into a care facility thereby providing the care facility with the ability to monitor the use of a fluid from the time it is prepared through to the time it is wasted. This information may be used for inventory analysis, to identify drug diversion, for patient billing purposes, and for other uses described herein.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 3A is a diagrammatic view of a plurality of operably connected fluid identification systems having various sensors for monitoring and tracking the use of a fluid in accordance with a representative embodiment of the present invention.

FIG. 4A is a perspective view of a sensor embedded within a syringe in accordance with a representative embodiment of the present invention.

FIG. 4B is a cross section view of the syringe of FIG. 4A in accordance with a representative embodiment of the present invention.

FIG. 10 is a cross section view of an attachment device prior to use, the attachment device having a sensor for identifying a fluid in accordance with a representative embodiment of the present invention.

FIG. 11 is a cross section view of an attachment device in use, the attachment device having a sensor for identifying a fluid in accordance with a representative embodiment of the present invention.

DETAILED DESCRIPTION OF THE INVENTION

Figure 1:
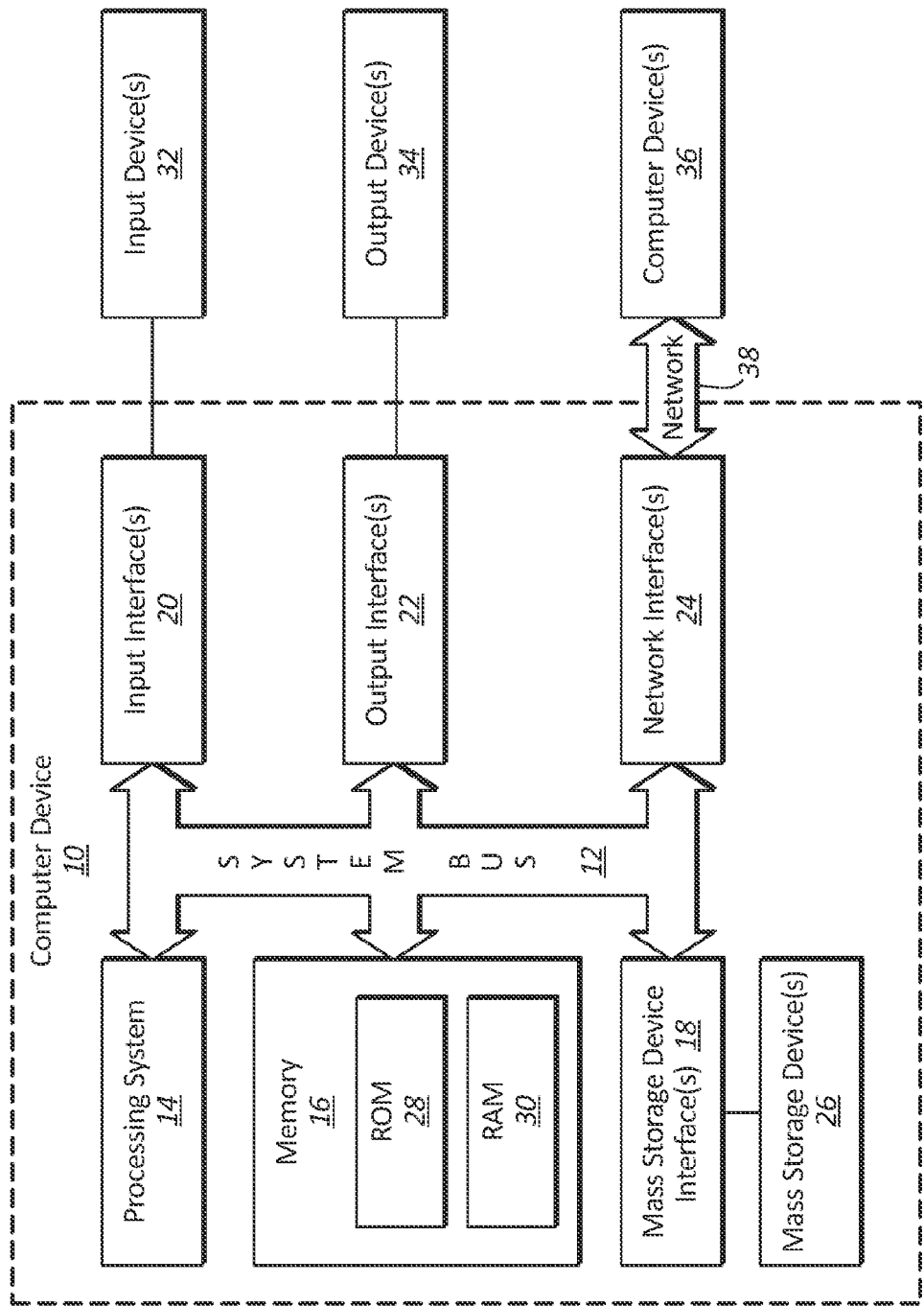
FIG. 1 shows a representative computer system suitable for use with embodiments of the invention.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention address the problem of tracking fluids, such as medicaments, used in acute care facilities. Thus, embodiments of the present invention provide systems, methods, and computer-readable media storing computer instructions for implementing methods for tracking and reporting the prescription, compounding, use, and wasting of fluids.

For convenience, the word "fluid" is used herein to refer to a liquid medicament or other liquid solution for which tracking is desirable in an acute care facility. This word, "fluid," is not intended to be limited to any drug type or classification, but is merely a word choice of convenience, and should be understood to apply to any type of fluid for which a tracking in accordance with the principles described herein. Therefore, unless the specific use of the word "fluid" herein is specific to a drug type or classification, the word should be read broadly as described.

Similarly, the word "sensor" is used herein to refer to any device that measures a physical quantity and converts it into a signal which can be read by an observer or by an instrument. This word, "sensor," is not intended to be limited to any specific type of technology or physical properties, but is merely a word choice of convenience, and should be understood to apply to any type of sensor which is compatible with the principles described herein. Therefore, unless the specific use of the word "sensor" herein is specific to a type of technology or physical property, the word should be read broadly as described.

In some embodiments, a fluid identification system is provided which identifies and tracks the prescription, use, and disposal of a fluid. In some instances, the fluid identification system comprises a single sensor associated with a device in which the fluid is stored or through which the fluid passes. For example, in some embodiments a fluid identification system is provided comprising a single sensor associated with an IV bag. In other embodiments, a fluid identification system is provided comprising a single sensor associated with a syringe. Further still, in some instances a fluid identification system is provided comprising a single sensor associated with at least one of an ampoule, a vial, and a disposal system used with the fluid.

A fluid identification system in accordance with the present invention may further include a plurality of sensors and devices, wherein each sensor is associated with at least one device in which the fluid is stored or through which the fluid passes. Further, the plurality of sensors and devices may be operably connected to a computer system or computer device having a computer-readable media for implementing methods for tracking and reporting the prescription, use, and wasting of a fluid. Accordingly, the fluid identification system of interconnected sensors may be used to track and verify the use of the fluid during its entire lifecycle between the plurality of devices.

FIG. 1 and the corresponding discussion are intended to provide a general description of a suitable operating environment in which embodiments of the invention may be implemented. One skilled in the art will appreciate that embodiments of the invention may be practiced by one or more computing devices and in a variety of system configurations, including in a networked configuration. However, while the methods and processes of the present invention have proven to be particularly useful in association with a system comprising a general purpose computer, embodiments of the present invention include utilization of the methods and processes in a variety of environments, including embedded systems with general purpose processing units, digital/media signal processors (DSP/MSP), application specific integrated circuits (ASIC), stand alone electronic devices, and other such electronic environments.

Embodiments of the present invention embrace one or more computer-readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer-readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system. While embodiments of the invention embrace the use of all types of computer-readable media, certain embodiments as recited in the claims may be limited to the use of tangible, non-transitory computer-readable media, and the phrases "tangible computer-readable medium" and "non-transitory computer-readable medium" (or plural variations) used herein are intended to exclude transitory propagating signals per se.

With reference to FIG. 1, a representative system for implementing embodiments of the invention includes computer device 10, which may be a general-purpose or special-purpose computer or any of a variety of consumer electronic devices. For example, computer device 10 may be a personal computer, a notebook computer, a netbook, a tablet computer such as the iPad® manufactured by Apple or any of a variety of Andriod™-based tablet computers produced by multiple manufacturers, a personal digital assistant ("PDA") or other hand-held device, a workstation, a minicomputer, a mainframe, a supercomputer, a multi-processor system, a network computer, a processor-based consumer electronic device, or the like.

Computer device 10 includes system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

Processing system 14 includes one or more processors, such as a central processor and optionally one or more other processors designed to perform a particular function or task. It is typically processing system 14 that executes the instructions provided on computer-readable media, such as on memory 16, a solid-state drive, a flash drive, a magnetic hard disk, a removable magnetic disk, a magnetic cassette, an optical disk, or from a communication connection, which may also be viewed as a computer-readable medium.

Memory 16 includes one or more computer-readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include solid-state drives, flash drives, hard disk drives, magnetic disk drives, tape drives and optical disk drives. A mass storage device 26 may read from and/or write to a magnetic hard disk, a removable magnetic disk, a magnetic cassette, an optical disk, or another computer-readable medium. Mass storage devices 26 and their corresponding computer-readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard and alternate input devices, such as a mouse, trackball, touch screen, light pen, stylus, or other pointing device, a microphone, a joystick, a game pad, a satellite dish, a scanner, a camcorder, a digital camera, and the like. Similarly, examples of input interfaces 20 that may be used to connect the input devices 32 to the system bus 12 include a serial port, a parallel port, a game port, a universal serial bus ("USB"), an integrated circuit, a Firewire® (IEEE 1394), or another interface. For example, in some embodiments input interface 20 includes an application specific integrated circuit (ASIC) that is designed for a particular application. In a further embodiment, the ASIC is embedded and connects existing circuit building blocks.

One or more output interfaces 22 may be employed to connect one or more corresponding output devices 34 to system bus 12. Examples of output devices include a monitor or display screen or other electronic display, a speaker, a printer, a multi-functional peripheral, and the like. A particular output device 34 may be integrated with or peripheral to computer device 10. Examples of output interfaces include a video adapter, an audio adapter, a parallel port, and the like. Examples of electronic displays include monitors, televisions, e-ink displays, projection displays, or any other display capable of displaying changing information under the control of a computer device.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system computer device 10 may participate in a distributed computing environment, such as a cloud-based computer environment, where functions or tasks are performed by a plurality of networked computer devices.

Figure 2:
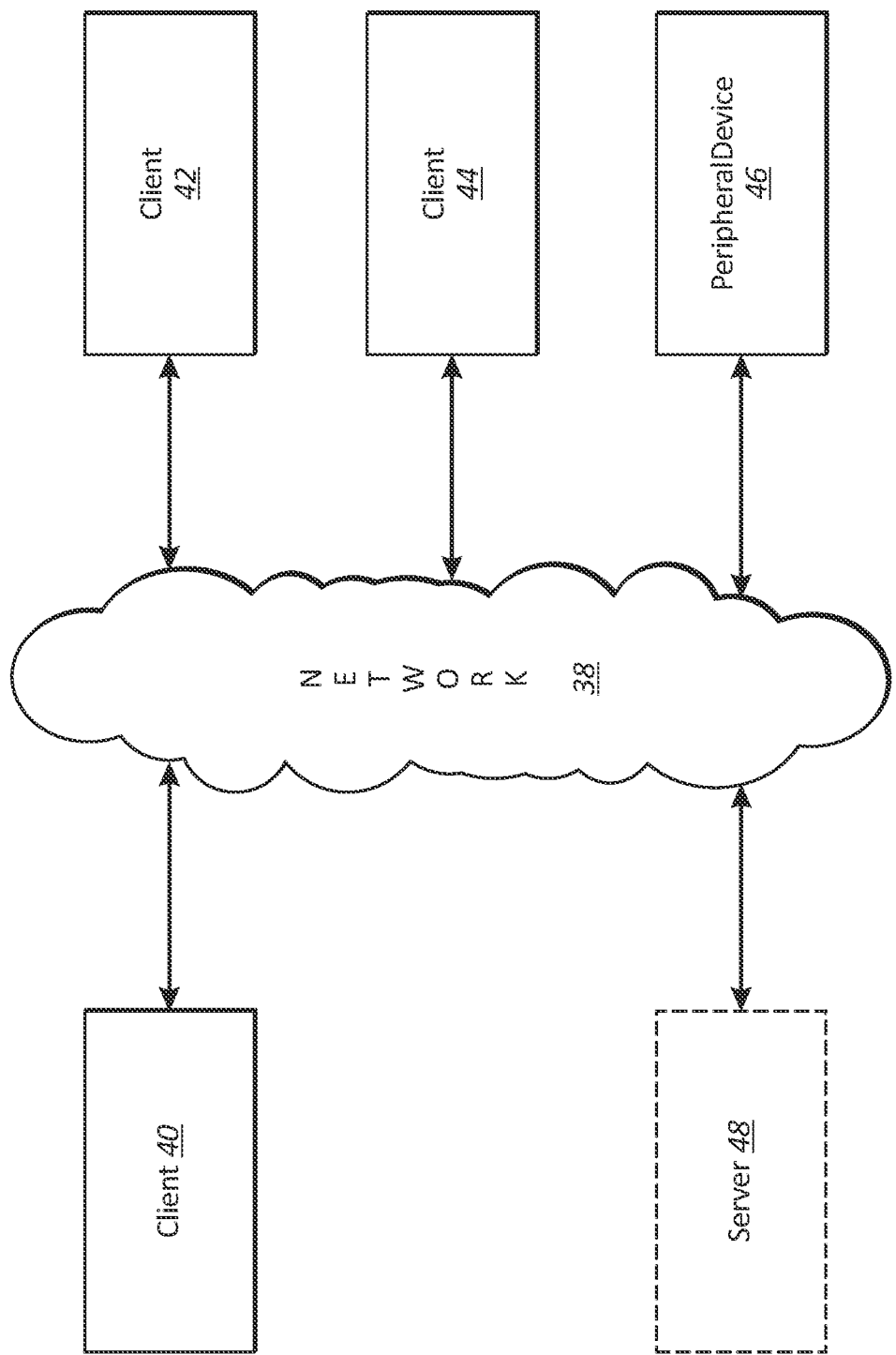
FIG. 2 shows a representative networked computer system suitable for use with embodiments of the invention.

Thus, while those skilled in the art will appreciate that embodiments of the present invention may be practiced in a variety of different environments with many types of system configurations, FIG. 2 provides a representative networked system configuration that may be used in association with embodiments of the present invention. The representative system of FIG. 2 includes a computer device, illustrated as client 40, which is connected to one or more other computer devices (illustrated as client 42 and client 44) and one or more peripheral devices (illustrated as multifunctional peripheral (MFP) MFP 46) across network 38. While FIG. 2 illustrates an embodiment that includes a client 40, two additional clients, client 42 and client 44, one peripheral device, MFP 46, and optionally a server 48, which may be a print server, connected to network 38, alternative embodiments include more or fewer clients, more than one peripheral device, no peripheral devices, no server 48, and/or more than one server 48 connected to network 38. Other embodiments of the present invention include local, networked, or peer-to-peer environments where one or more computer devices may be connected to one or more local or remote peripheral devices. Moreover, embodiments in accordance with the present invention also embrace a single electronic consumer device, wireless networked environments, and/or wide area networked environments, such as the Internet.

Similarly, embodiments of the invention embrace cloud-based architectures where one or more computer functions are performed by remote computer systems and devices at the request of a local computer device. Thus, returning to FIG. 2, the client 40 may be a computer device having a limited set of hardware and/or software resources. Because the client 40 is connected to the network 38, it may be able to access hardware and/or software resources provided across the network 38 by other computer devices and resources, such as client 42, client 44, server 48, or any other resources. The client 40 may access these resources through an access program, such as a web browser, and the results of any computer functions or resources may be delivered through the access program to the user of the client 40. In such configurations, the client 40 may be any type of computer device or electronic device discussed above or known to the world of cloud computing, including traditional desktop and laptop computers, smart phones and other smart devices, tablet computers, or any other device able to provide access to remote computing resources through an access program such as a browser.

Referring generally to FIGS. 3-22, various representative embodiments of a fluid tracking system and methods to monitor and track the use of intravenous (IV) fluids and liquid oral medications (herein referred to simply as fluids or IV fluids) is shown. Referring now to FIG. 3A, a representative fluid tracking system 120 is shown. In some embodiments, a fluid tracking system 120 is provided or established within a single care facility, such as a hospital, or it may be used in a group of various related facilities, such as an off-site pharmacy, a remote doctor's office, and a hospital (or other care facility) to monitor or track the use of various fluids.

In hospitals and other care facilities, a common practice is for a physician to prescribe a fluid to a patient that is administered intravenously. Some fluids comprise one or more drugs which are determined to diagnose cure, mitigate, treat, or prevent a disease or other illness. In some embodiments, a desired drug is compounded into an IV fluid by combining the drug with a diluent. Once compounded, the fluid is placed into a container 122, such as a syringe, an IV bag, an ampoule, a vial, an auto-injector container, or another such container which is needed to administer the fluid to a patient. In some instances, the use of the fluid is monitored by tracking the container 122 in which the fluid is stored. For example, in some embodiments the compounded fluid is initially monitored at the point of time in which the compounded fluid is placed in container 122. Subsequent uses of the fluid are further tracked using container 122, such as when the compounded fluid is administered to the patient or wasted following administration to the patient. Thus, a care facility is able to track the compounded fluid and identify potential medication errors, administration errors, and drug diversion. Monitoring of the compounded fluid may also be beneficial for inventory management and patient billing purposes.

In some embodiments, a fluid tracking system 120 is provided which includes a plurality of fluid identification stations 140, 142 and 144. Fluid identification stations are generally provided at key locations where it is beneficial to know the identification, status, and other characteristics of a desired fluid. Non-limiting examples of key locations where a fluid identification station may be provided include a pharmacist's laboratory, a stockroom where a fluid is stored, a nurse's station, a patient's room, and a fluid disposal station.

In some embodiments, fluid identification stations 140, 142 and 144 are operably interconnected via a computer network 146. When information is acquired by a fluid identification station, the information is transmitted to the computer network 146 where the information is made accessible to the remaining fluid identification stations. Further, in some embodiments acquired information is stored in a database, such as an electronic medical record (EMR) 148.

EMR 148 generally comprises a computerized medical record for a patient, as known in the art. In some embodiments, EMR 148 is configured to receive and store information relating to a fluid detected and tracked by fluid tracking system 120. EMR 148 may further include general information relating to the treatment of the patient, such as the patient's medical history, patient contact information, and patient insurance and billing information. In some embodiments, the EMR 148 further comprises an electronic medication administration record (EMAR) which includes specific information relating to the administration of medications to a patient. Accordingly, in some embodiments information relating to a fluid detected and tracked by fluid tracking system 120 is integrated into the EMAR of EMR 148. Further, information stored in the EMAR may be accessible to fluid tracking system 120, thereby enhancing the detection and tracking capabilities of fluid tracking system 120.

Computer network 146 may include a server on which a computer executable program is loaded having instructions for receiving, analyzing, and storing information received from fluid identification stations 140, 142 and 144. The computer network 146 may further include network security software or other precautionary software as may be required to comply with Health Information Patient Privacy Act requirements. In some embodiments, computer network 146 comprises a local area network. In other embodiments, computer network 146 is a global area network.

In general, a fluid identification station comprises one or more sensors for detecting a characteristic of a desired fluid. For example, a fluid identification station may include a sensor for detecting a temperature, a chemical constituent, a concentration, a volume, an age or expiration, a flow rate, and/or a contamination of the fluid. The fluid identification station further comprises a computer device or other processor unit having capabilities for receiving and transmitting data received from the sensor. Accordingly, a fluid identification station in accordance with the present invention comprises at least one means of detecting or identifying a fluid, and at least one means of communicating the detection or identification of the fluid to a user.

Figure 3B:
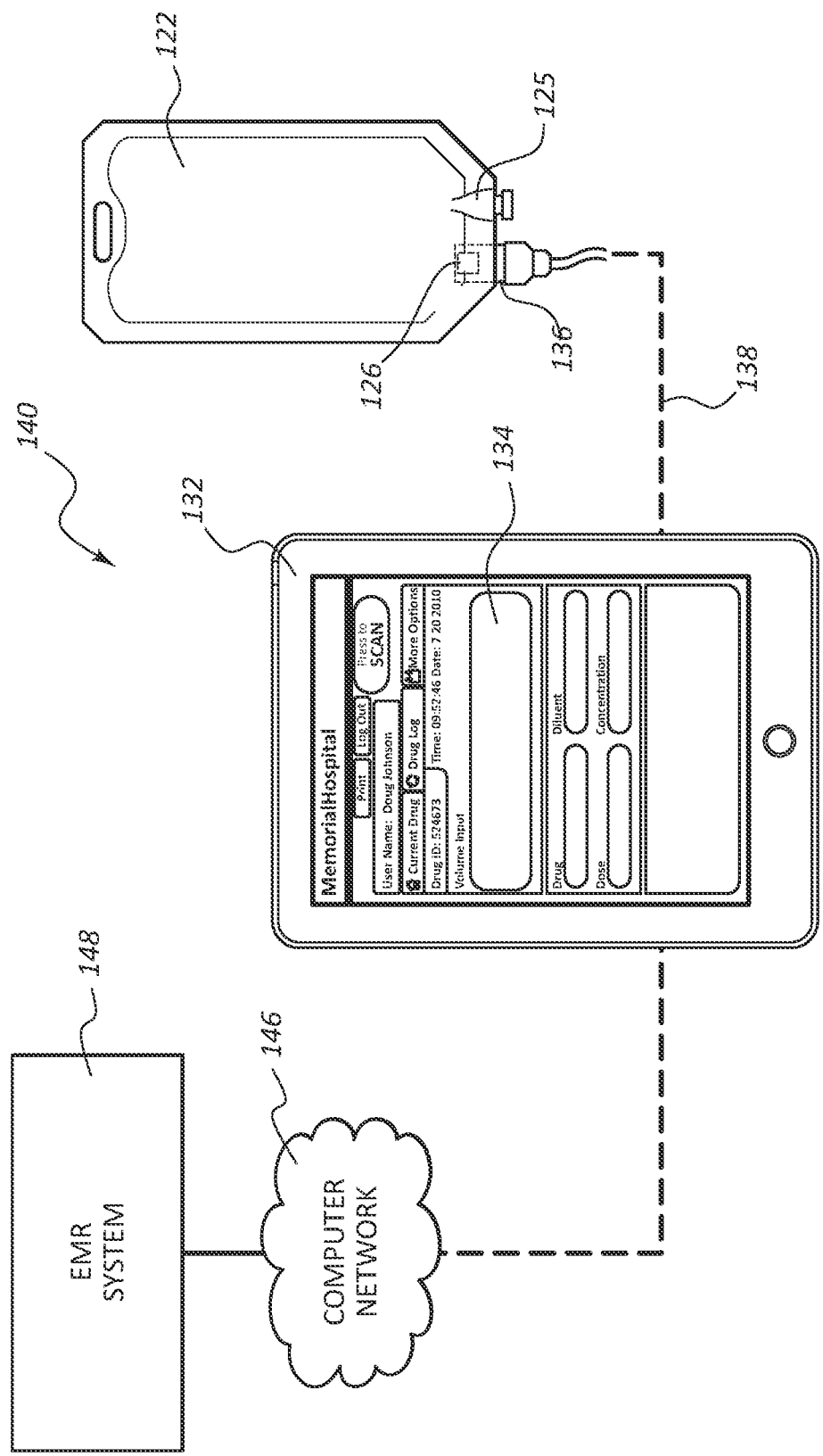
FIG. 3B shows a fluid identification system in accordance with a representative embodiment of the present invention.

Referring now to FIGS. 3A and 3B, in some embodiments a fluid tracking system 120 is provided having a first fluid identification station 140. First fluid identification station 140 is provided as a means for tracking a fluid stored in a container 122. In some embodiments, container 122 comprises a sensor 126 that is configured to identify at least one fluid characteristic of a fluid stored in container 122. Sensor 126 further comprises a sensor element 128 which is positioned on sensor 126 so as to be in direct contact with a fluid stored in container 122. For example, in some embodiments sensor 126 is embedded within container 122 such that sensor element 128 is exposed to a fluid within container 122. Container 122 may further include means for communicating data from sensor 126 to a computer device or processor unit 132. As shown, sensor 126 of first fluid identification station 140 is embedded within container 122 and electronically, wirelessly or otherwise operably coupled to processor unit 132.

Sensor element 128 is configured to detect at least one fluid characteristic. Thus, the function of sensor 126 is determined by the capabilities of sensor element 128. In some embodiments, sensor 126 comprises a plurality of sensor elements 128. Thus, sensor 126 may be multifunctional or capable of detecting multiple fluid characteristics. In other embodiments, first fluid identification station 140 comprises a plurality of sensors 126.

As configured, first fluid identification station 140 is capable of identifying a fluid stored in container 122 and detect various fluid characteristics, as may be desired. For example, in some embodiments a physician prescribes a fluid to a patient and then updates the patient's EMR to indicate the prescribed fluid. The physician then orders the fluid from the pharmacy. The pharmacy receives the physician order and prepares the compounded fluid based upon information contained in the patient's EMR. Once prepared, sensor 126 of first fluid identification system 140 identifies the compounded fluid and compares the fluid characteristics of the compounded fluid with the information contained in the patient's EMR. Thus, first fluid identification system 140 is able to identify the fluid and record any discrepancies or other errors that may be present by comparing data from the system's sensor 126 and the order originally made by the physician.

In some embodiments, first fluid identification system 140 further comprises an alert system, wherein upon detection of an error or other discrepancy, first fluid identification system 140 creates and records an error code. First fluid identification system 140 then alerts a designated authority or other user of the error. In some embodiments, the creation of an error code prevents subsequent use of the compounded fluid wherein the remaining fluid identification systems 142 and 144 receive or otherwise access the error code and execute protocols for refusing administration or use of the compounded fluid.

In some embodiments, fluid tracking system 120 identifies and records information regarding the identity of the fluid. For example, in some embodiments the identification of a fluid is recorded along with other relevant information, such as the initial volume of the fluid, an identification of the container, the identity of the pharmacist who prepared the fluid, and the drug lot number for manufacture. In other embodiments, the fluid tracking system 120 identifies and records multiple fluids being administered to a patient, the dose for concentration of the fluids, the flow rate of the fluids, a volume of fluid being administered to the patient, and/or the temperature of the fluid. This information may be stored by the computer network 146, wherein the information is made available for subsequent access by a user or an additional fluid identification station of the fluid tracking system 120. In some embodiments, this information is stored in a patient's EMR 48.

Referring now to FIG. 3A, in some embodiments fluid tracking system 120 further comprises a second fluid identification station 142. Fluid identification station 142 is provided to monitor and detect a fluid during an infusion procedure via an intravenous fluid delivery system 150. During an infusion procedure, an intravenous fluid is introduced into a patient via a catheter 152 or other such device of the intravenous fluid delivery system 150. Fluid identification station 142 further comprises a sensor 126 and sensor element 128 coupled to the intravenous fluid delivery system 150 to monitor the intravenous fluid as it flows therethrough. In some embodiments, data acquired from sensor 126 of station 142 is compared with a data from fluid identification system 142 to detect any discrepancies in the identification or prescribed therapy of the fluid. As such, fluid tracking system 120 can thus identify the intravenous fluid and recognize discrepancies between the intravenous fluid being administered and the original order prescribed by the physician.

In some embodiments, fluid tracking system 120 further comprises a third fluid identification station 144. Fluid identification station 144 is provided to monitor and detect a fluid during the process of wasting or disposing the fluid following a prescribed use. In some embodiments, fluid identification station 144 comprises a sensor 126 and a sensor element 128 coupled to a waste disposal unit 160 such that sensor element 128 is in the pathway of the fluid as the fluid is being disposed. Fluid identification station 144 is thus provided to identify the wasted fluid and record the contents and characteristics of the fluid. In some embodiments, fluid identification station 144 identifies the volume of the wasted fluid along with the identity of one or more drugs within the fluid and the concentration of such drugs. Fluid identification station 144 may further access and compare fluid data from fluid identification stations 140 and 142 as stored on computer network 146. Thus, fluid identification station 144 may confirm the proper use of the fluid and identify any impermissible diversions, theft or other illegal modifications of the fluid.

Fluid identification stations 140, 142 and 144 generally form a closed-loop fluid monitoring system 120 that identifies and records the preparation, use, wasting or re-dispensing of a fluid. Thus, the lifecycle of a fluid may be monitored and tracked to verify proper preparation, use and wasting of the fluid. The monitoring features of the present invention may be useful where a fluid is identified as being particularly sensitive or dangerous, such as where the fluid contains a narcotic or other potentially harmful component. Further, the monitoring and tracking features of the present invention may be useful for inventory and billing purposes.

As previously discussed, the various fluid identification stations of the present invention include at least one sensor 126 having a sensor element 128 which is configured to identify one or more characteristics of a fluid or a fluid component. In some embodiments, a fluid identification station of the present invention includes a sensor as disclosed in International Application Number WO 2009/114115, published Sep. 17, 2009, which is incorporated herein by reference. Sensor element 128 is generally positioned such that a sensing surface of a sensor element 128 interacts with the fluid of interest. In some embodiments, the sensor element 128 comprises an electrode. In other embodiments, the sensor 126 comprises a semiconductor device mounted on a printed circuit board or other substrate. Further still, in some embodiments sensor 126 and sensor element 128 are powered with an external source.

The fluid identification stations of the present invention further comprise at least one processor unit 132 which is configured to receive sensing measurements or data from the sensor 126. In some embodiments, processor unit 132 further comprises computer software to enable processor unit 132 to interpret the sensing measurements and identify a desired characteristic of the fluid.

For example, sensor 126 may be configured to sense one or more parameters or characteristics of a fluid by performing one or more tests. Data resulting from the tests performed by sensor 126 are transmitted to processor unit 132 where the data is processed or analyzed to determine a characteristic of the fluid.

Sensor 126 may be configured to sense or detect any characteristic of a desired fluid. In some embodiments, sensor 126 is configured to sense the impedance of a fluid. For example, an electrical signal may be driven through the sensor elements 128 of sensor 126 into the fluid at a range of frequencies. Sensor element 128 may then measure the current generated in the fluid. The measured current may then be conditioned or processed by at least one of the sensor 126 and the processor unit 132. Data received or sensed by sensor 126 may further be used to form frequency dependent maps of the impedance of the fluid. The maps, or fluid signatures, may be unique to each fluid of interest, its concentration, its component, its purity and its state of degradation. In some embodiments, processor unit 132 compares the fluid signature of a fluid to a library of preloaded fluid signatures to aid in identifying the fluid or a characteristic of the fluid. In some configurations, sensor 126 utilizes one or more alternative or additional sensing methods to sense one or more parameters or characteristics of a fluid.

For example, in some embodiments a fluid tracking system 120 in accordance with the present invention uses a multi-parametric approach to identify the contents and characteristics of a fluid. In such an approach, multiple parameters (e.g. multiple fluid properties such as without limitation refractive index, electrochemical potential, impedance, admittance, conductivity, etc.) are sensed, and the combination of said sensed parameters are correlated to obtain a resolution of the various components within a fluid. For example, a fluid may be sensed with multiple sensors 126 (or with a sensor 126 having multiple sensor elements 128) and/or with multiplexing of a sensor element 128 to obtain independent sensing measurements. Such multi-parametric approaches advantageously provide for improved resolution of components within a fluid.

Sensor 126 may be electronically coupled to the processor unit 132 via a communication link 138, through which the processor unit electronically communicates with and/or electronically powers the sensor 126. For example, communication link 138 may include a wireless link (e.g., WiFi, Bluetooth®, WiMax, IR, RF, or other known wireless communication approaches), a direct wired connection (e.g. electrical wire or optical cable), or a direct connection via one or more direct lead contacts.

For embodiments where the sensor 126 is electronically coupled to processor unit 132 via a direct-wired or direct-lead connection, sensor 126 may further be electronically coupled to a connector member 136. Connector member 136 may include one or more lead contacts to establish an electrical connection to sensor 126. In some embodiments, connector member 136 extends outwardly from a container 122 such that connector member 136 is accessible from the exterior of container 122. As such, a user is able to couple an electrical cable to connector member 136 and establish a wired connection therebetween. In some embodiments, the wired connection includes a cable that is coupled to an input interface of the processor unit 132. Such input interface can include a USB other suitable port (not shown). In some embodiments, sensor 126 is electronically powered via one or more power lines coupled to the direct-wired connection.

In other embodiments, sensor 126 is electronically powered via a separate power supply coupled to container 122. For example, in some embodiments one or more power sources are coupled to container 122 and electronically coupled to sensor 126 to power sensor 126, such as a battery. In other embodiments, sensor 126 is powered wirelessly, such as via a wireless radio frequency (RFID) technology. An example of a sensor powered with RFID technology is described in United States Patent Application No. 2008/0129475, which was published Jun. 5, 2008, and which is incorporated herein by reference in its entirety.

With continued reference to FIGS. 3A and 3B, processor unit 132 generally includes a computer system in which some or all of the processing logic can be implemented for identifying the contents and characteristics of a fluid. Processor unit 132 may further be incorporated or integrated into another device or computer system. For example, processor unit 132 may be into a smart pump, an automated dispensing cabinet (ADC), a bedside computer system, or other suitable computer system or fluid-interacting device.

In some embodiments, processor unit 132 comprises computer-executable instructions configured to cause the processor to execute functions for implementing logical operations. For example, in some embodiments computer-executable instructions are provided to implement a process for processing, storing, displaying or transmitting data relating to the identity of one or more components of a fluid.

In some embodiments, processor unit 132 further comprises an integrated display device 134. In other embodiments, processor unit 132 is operably coupled to a separate display device (not shown). Display device 134 may include any variety of display devices, such as a liquid crystal display (LCD) device, a cathode ray tube (CRT) display device, plasma display panel (PDP), light emitting diode (LED) display, or other such display devices known in the art. In some embodiments, display device 134 is a bedside display located at the point of care of a patient. Such bedside displays are commonly located in hospitals and other care facilities. As such, display device 134 is positioned in close proximity to the patient. In some embodiments, a display device 134 is connected to an IV pole or wall within a patient's room. Display device 134 is further coupled to processor unit 132 and/or an information technology infrastructure of a care facility.

Some embodiments, display device 134 displays information related to the identity of a fluid detected by a fluid identification station of fluid tracking system 120. Display device 134 may further display patient information, medication administration history, information regarding the safety status of a drug, information regarding the status of proper administration of the fluid, information regarding alerts or warnings related to the administration of a fluid to a patient, date, time, location, and other patient-related, facility-related, or treatment-related information.

In some embodiments, processor unit 132 further comprises a graphical user interface (GUI) 134 that displays the identity of a fluid. GUI 134 may be configured to display any information which may be desired in treating a patient. In some embodiments, GUI 134 further comprises a touch-screen display having input regions wherein a user can input data relating to the treatment of a patient. Processor unit 132 may further include a push button or other means whereby a user can initiate a scan to detect a fluid in container 122. For example, in some embodiments container 122 comprises a barcode or other computer recognizable code containing information relating to the contents of the container (not shown). A scanning function of processor unit 132 may be used to scan or otherwise detect information contained in the computer recognizable code. Once detected, processor unit 132 may then compare sensing measurements received from the sensor 126 to information contained in the computer recognizable code to further verify the contents of container 122.

Referring now to FIGS. 4A and 4B, sensor 126 may further be disposed within a syringe 170. In some embodiments, sensor 126 is at least partially embedded within a plunger component 172 of syringe 170 such that sensor element 128 is exposed to fluid chamber 186. For example, the sensor 126 and sensor element 128 are embedded into stopper 174 of plunger component 172. In other embodiments, sensor 126 is embedded with another portion of the syringe 70, such as the inner surface 188 or distal spout 189 of syringe 170.

In some embodiments, sensor 126 is coupled to connection member 136 via an electrical line 154. Connector member 136 may be positioned on an outer surface of syringe 170 thereby providing an operably connection between sensor 126 and an external device, such as processor unit 132.

Figure 5:
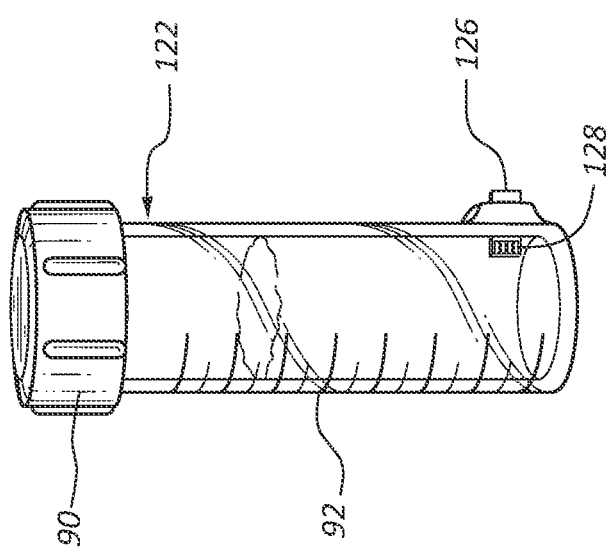
FIG. 5 is a perspective view of a sensor embedded within a vial in accordance with a representative embodiment of the present invention.

Referring now to FIG. 5, in some embodiments container 122 comprises a vial having a sensor 126 and sensor element 128 incorporated therein. As shown, sensor 126 and sensor element 128 may be embedded into a body portion 192 of container 122. In other embodiments, sensor and sensor element 126 and 128 are embedded within a cap 190 of container 122.

Figure 6:
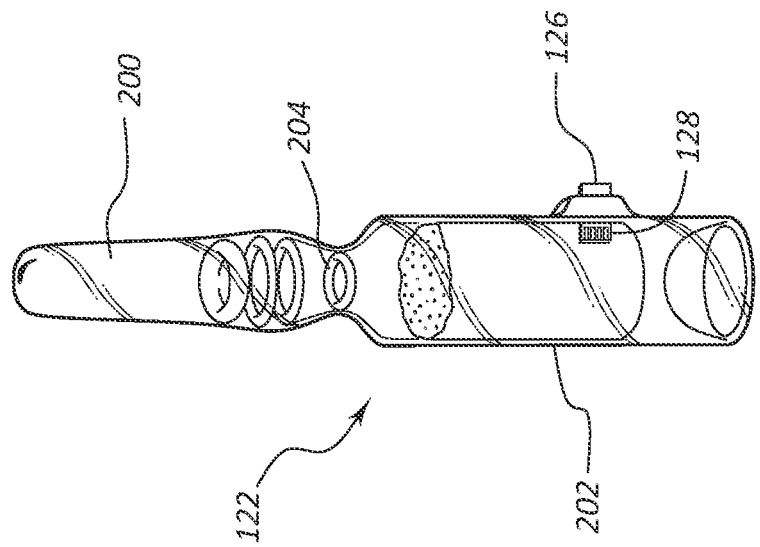
FIG. 6 is a perspective view of a sensor embedded within an ampoule in accordance with a representative embodiment of the present invention.

Referring now to FIG. 6, in some embodiments container 122 comprises an ampoule having a sensor 126 and sensor element 128 incorporated therein. As shown, the sensor 126 and sensor on the 128 may be embedded into a body portion 202 of container 122. In other embodiments, sensor and sensor element 126 and 128 are embedded within a top portion 200 of container 122, wherein container 122 further comprises a breakable portion 204 interposed between top portion 200 and body portion 202.

Figure 7:
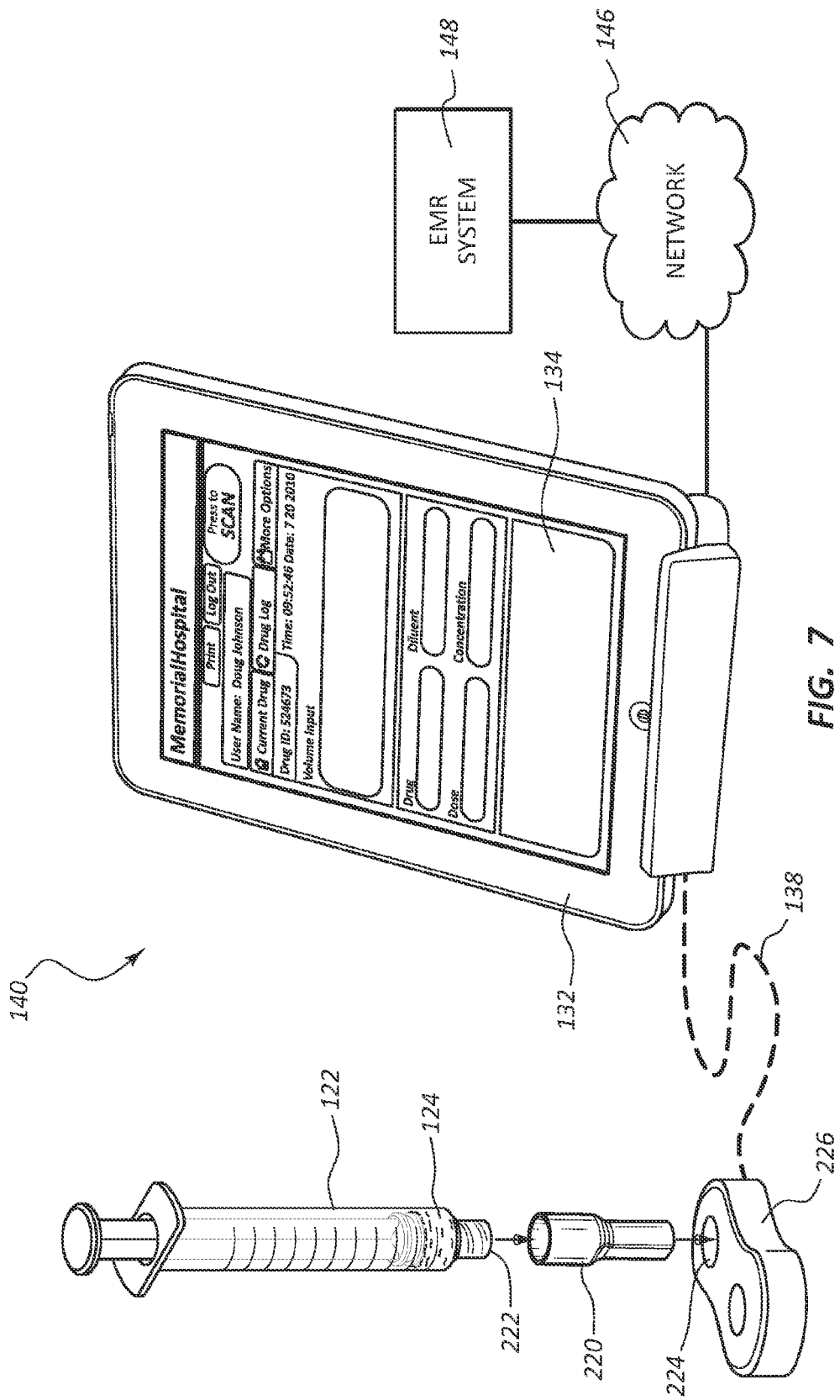
FIG. 7 is a perspective view of a fluid identification system in accordance with a representative embodiment of the present invention.
Figure 8:
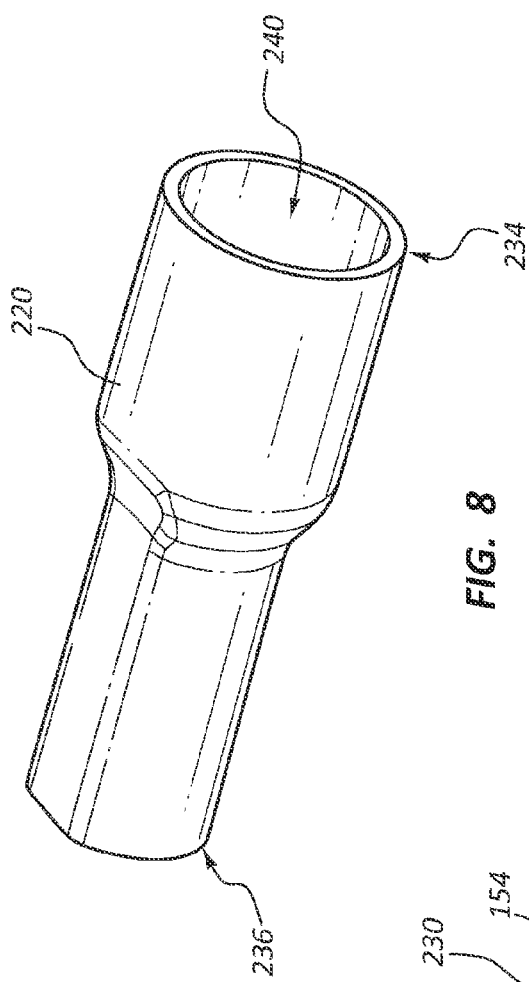
FIG. 8 is a perspective view of an attachment device having a sensor for identifying a fluid in accordance with a representative embodiment of the present invention.
Figure 9:
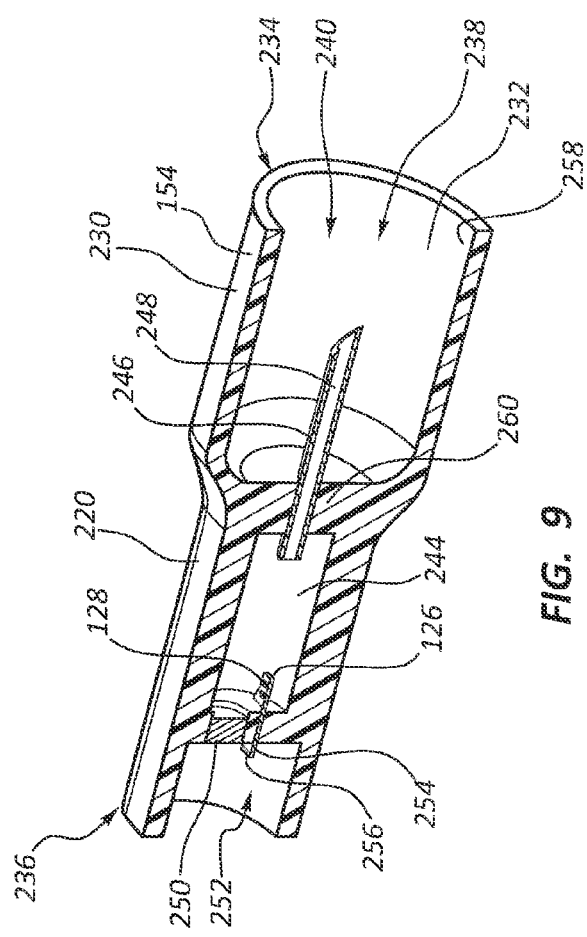
FIG. 9 is a cross section view of the attachment device of FIG. 8.

In some embodiments, fluid identification station 140 further comprises an attachment device 220, shown in FIG. 7-9. Attachment device 220 generally comprises an adapter configured to selectively attach to an opening 222 of a container 122 and further attach to a secondary device, such as a receptacle 224 of a receiving unit 226. In some embodiments, attachment device 220 is a cap, a stopper, a vial, or a Luer connector (such as the Q-Syte™ connector from Becton, Dickinson and Company). In other embodiments, the attachment device 220 further comprises an intravenous spike whereby to couple attachment device 220 to an intravenous fluid bag.

In some configurations, sensor 126 is operably coupled to processor unit 132 via receiving unit 226. Receiving unit 226 comprises a receptacle 224 which is configured to receive attachment device 120. Receptacle 224 may include any shape and size configured to compatibly receive attachment device 220. In some embodiments, receptacle 224 further comprises at least one electrical contact (not shown) that is configured to contact at least one electrical contact (not shown) located on opening 222 of container 122. As such, fluid data or sensing measurements received by attachment device 220 is communicated to processor unit 132 via receiving unit 226. Processor unit 132 is then able to identify the various constituents and characteristics of the fluid in container 122, as described above.

In some embodiments, receiving unit 126 is further configured to provide electrical power to the sensor 126 of attachment device 220. Accordingly, receiving unit 126 may further affect as an external power supply for attachment device 220, thereby providing the power necessary for the sensor 126 and sensing element 128 to detect the identity and/or other characteristics of a fluid in container 122.

Referring now to FIGS. 8 and 9, attachment device 120 may further include an attachment body 230 having a first end 234 and a second end 236. In some embodiments, first end 234 is configured to selectively attach to a surface of container 122. For example, in some embodiments first end 234 comprises an opening 238 configured to receive a surface of container 122, such as a nozzle of a syringe. In some instances, opening 238 further comprises a feature for selectively retaining a surface of container 122, such as a set of threads or a detent. First end 234 may further include a feature, such as an IV spike 246, for facilitating coupling between attachment device 220 and an intravenous fluid bag (not shown). IV spike 246 further comprises a fluid channel 248 to facilitate communication of a fluid between the proximal fluid chamber 232 and internal chamber 244.

Second end 236 is further configured to selectively connect to the processor unit 132 directly or indirectly, such as by being connected via receiving unit 126. An internal chamber 144 of attachment body 230 further comprises a sensor 126 having one or more sensing elements 128. As with the previous embodiments, sensing elements 128 are positioned within internal chamber 244 so as to be in fluidic communication with a fluid present was in internal chamber 244.

In some configurations, the second end 236 of the attachment body 230 further includes an electrical connector 254 is configured to selectively connect to processor unit 132. Electrical connector 254 may include one or more contact surfaces 256 that are capable of forming a direct lead connection with another device, such as receiving unit 226, as discussed above. Electrical connector 254 may further be disposed on another portion of the attachment body 230, such as an inside or outside surface of the attachment device 220.

In some embodiments, internal chamber 244 of the attachment body 230 is configured to retain liquid when attachment body 230 is attached to a container 122. Internal chamber 244 is further configured to be entirely closed such that fluid stored within internal chamber 244 is prevented from leaking out of second end 236 when first end 234 is coupled to a container 122. In other configurations, the internal chamber 244 is separated from the cavity 240 via one or more complete or partial barriers 260.

In some embodiments, the attachment device 220 further comprises a membrane 250 interposed between internal chamber 244 and the external environment. In some instances, membrane 250 is air permeable but impermeable to fluid. For example, in some embodiments membrane 250 is hydrophobic yet comprises a plurality of pores sufficient to permit passage of air while preventing the passage of fluids. As such, when a fluid flows into internal chamber 244, air is able to flow out of membrane 250, while retaining the fluid in internal chamber 244. In other embodiments, membrane 250 is replaced with small holes that extend between the internal chamber 144 and the exterior environment. These holes can be small enough and have enough surface areas that a fluid cannot enter therein, but air can escape therethrough.

Referring now to FIGS. 10 and 11, an attachment device 220 of the present invention is shown in use. With reference to FIG. 9, attachment body 230 is brought into proximity with an opening of a container 122. This opening may include a portion or surface 162 of an IV bag that is intended to be pierced via an IV spike 246. Portion 162 of container 122 may include any shape and size to facilitate selective attachment of container 122 to attachment device 220. As shown, in some embodiments portion 262 is shaped and sized to press fit within the cavity 240 in the opening 238 of first end 234 of attachment device 220.

FIG. 11 illustrates the attachment device 220 following attachment of portion 262 to opening 238 of attachment device 220. Following attachment, a fluid from a container 122 is permitted to flow into internal chamber 244 via IV spike 246. As fluid flows into the internal chamber 244 from internal chamber 244, air is expelled from internal chamber 244 via membrane 250. The fluid within internal chamber 244 is then sensed by sensor element 128. Data and/or results from sensor 126 are received by processor unit 132 while attachment device 220 is coupled to container 122. Once the fluid is identified, container 122 may be detached from attachment device 220.

Figure 12:
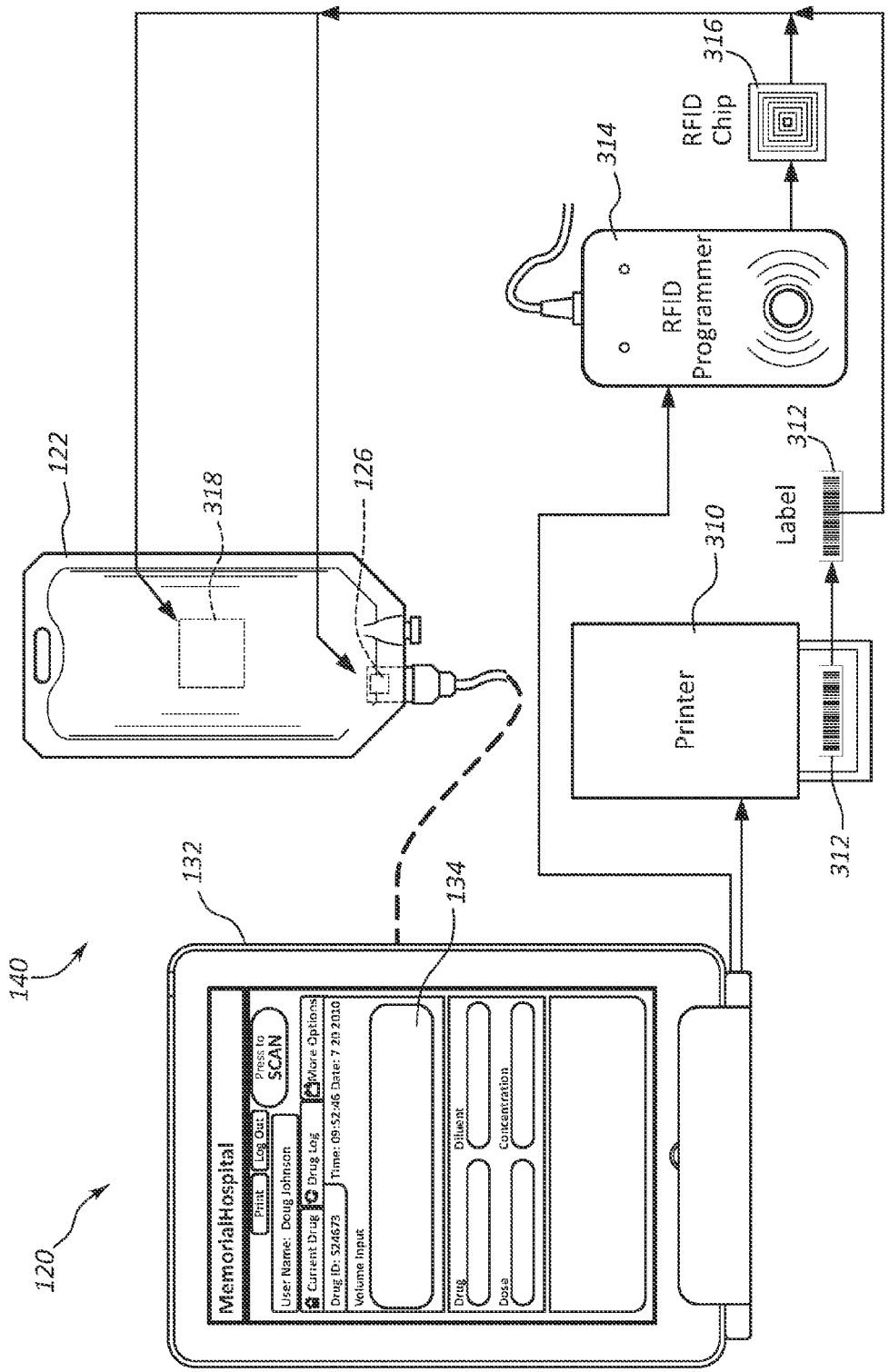
FIG. 12 is diagrammatic view of a fluid identification system operably coupled to a computer device and various output devices in accordance with a representative embodiment of the present invention.

Referring now to FIG. 12, an alternative embodiment of fluid identification station 140 is shown. Following identification of the contents and characteristics of a fluid by fluid identification station 140, the results may be displayed, crosschecked, and recorded by various components of station 140. For example, the identity or other characteristic of a fluid may be communicated to a user through a display device 134. The user may then verify the compounded fluid has the same contents and characteristics as that prescribed by a requesting physician or as indicated in the patient's EMR.

In some instances, a fluid identification station 140 further comprises a printer 310 which may be used to print out a label 312 that can be affixed to the container 122 (shown as attachment 318 on container 122), wherein the label 312 comprises information which identifies the fluid or at least one characteristic of the fluid. For example, label 312 may include a barcode or other machine recognizable code containing information relating to the identity or other characteristics of a fluid in container 122. In some embodiments, fluid identification station 140 automatically prints label 312 thereby avoiding human error which may occur when manually creating a label for container 122.

In some instances, a fluid identification station 140 further comprises an RFID programmer for creating an RFID chip 316 which may be attached to container 122 (shown as attachment 318 on container 122), wherein chip 316 comprises information which identifies the fluid or at least one characteristic of the fluid. In some embodiments, use of barcode 312 and/or RFID chip 316 permit a nurse or other care provider to automatically read the contents of container 122 by scanning the attached barcode or RFID chip 318 on the container 22, and subsequently scanning a barcode on a patient's wristband. Accordingly, in some embodiments a printer 310 or an RFID programmer 314 is electronically coupled to the processor unit 132 and configured to print a label 312 having a barcode or RFID chip 316 that contains information that is retrievable by a user.

In some embodiments, barcode 312 and/or RFID chip 316 may further include information about the fluid in the fluid container 122, such as the identity of a fluid manufacturer, a fluid lot number, a fluid catalog number, and expiration date of a fluid. Barcode 312 and RFID chip 316 may further include patient information which is determined to be useful in providing care to a patient. For example additional patient information may include the patient's name, age, weight, sex, and medicinal or food allergies. In some embodiments, barcode 312 and RFID chip 316 further include additional information which is determined to be useful in providing care to a patient. Such information may include a list of the patient's prescribed medications, dosage schedules, the identity and characteristics of a particular constituent of a fluid, such as a drug, a diluent, the concentration, a lot number, drug manufacturer, the identity of the clinician who prepared the fluid and/or verified a drug concentration within the fluid, the date and time when the fluid was prepared, and the temperature history and/or light exposure history of the fluid.

In some embodiments, prior to administering a fluid to a patient, a care provider utilizes a first fluid identification station 142 identify the contents and characteristics of the a fluid in a container 122. When fluid identification station 140 is used at a patient's bedside, the patient's information can be communicated to the care provider through a display device 134. Fluid identification station 140 may further access additional information about the patient or the fluid from computer network 146 and or the patient's EMR 148. Fluid identification station 140 may further be used to print out a record or report for use by the care provider to verify that the identified drug matches the prescribed medication. When the sensor system is configured to communicate with the patient's EMR, it may automatically perform a verification of the container's contents against the medication profiled for the patient.

As previously discussed, the methods of fluid identification described herein can include certain notice features (e.g., alarm) to alert a pharmacist, nurse, clinician, or other care provider concerning a potential harm or danger to the patient. Such notice can alert the pharmacist or the care provider to the error so that it may be corrected. In this manner, the present devices, systems, and methods can detect drug preparation errors before they result in harmful medication errors.

Figure 13:
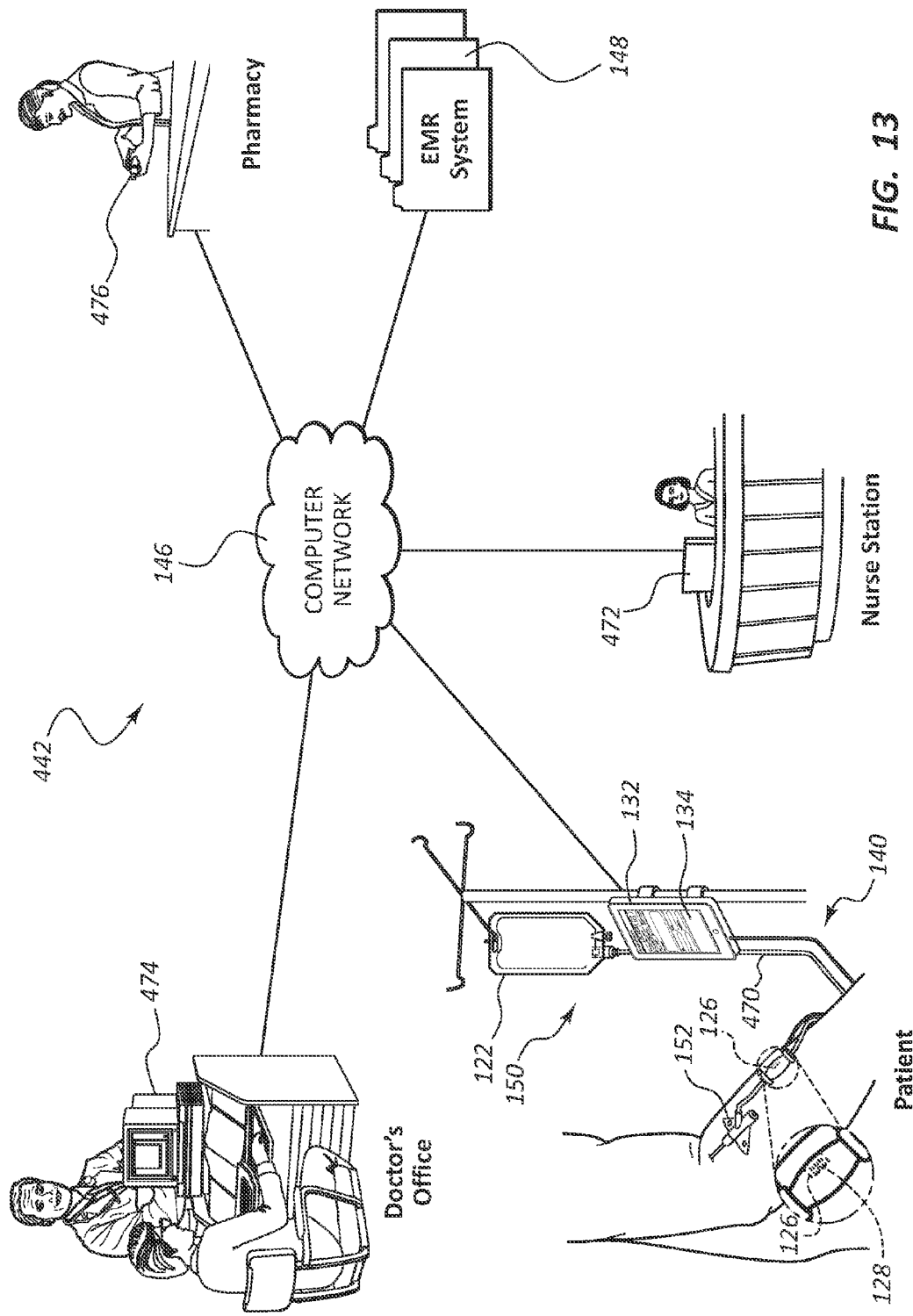
FIG. 13 is a diagrammatic view of an IV administration monitoring system comprising a plurality of fluid identification systems in accordance with a representative embodiment of the present invention.

Referring now to FIG. 13, an IV administration monitoring system 442 is shown. System 442 is configured to monitor the administration of the fluid into a patient and detect administration errors. In some embodiments, system 442 is further configured to record information about medicinal administration in the patient's EMR 148 or other such system which is configured to provide an automatic record of the administration. The ability to provide this record automatically can reduce the paperwork requirements currently imposed on nurses or other care providers. Such information may further be used to verify the contents and quantities of fluids designated for wasting in a fluid wasting system 444. Further still, such information may be used for charging and billing purposes. For example, the patient may be charged only for the volume of fluids and drugs actually administered to the patient, even when larger quantities of that fluid were delivered to the patient's room but were not used.

In some embodiments an IV administration monitoring system 442 is used to monitors an IV fluid during an infusion procedure via an IV fluid delivery system 150. During administration, IV fluid is placed into a container 122, such as a syringe, an IV bag, an ampoule, a vial, an auto-injector container, or other such container used in drug administration. The IV fluid is administered through the intravenous fluid administration system 150, which can include one or more IV tubes, a pump set, an IV extension set 470, a catheter 152, one or more needleless connectors, and other known components.

In some embodiments, IV administration monitoring system 442 further includes a sensor 126 coupled to the IV fluid delivery system 150. Sensor 126 may further include one or more sensing elements 128, as previously discussed. Sensor 126 can be coupled to or embedded in any component of the IV fluid delivery system 150. For example, sensor 126 can be disposed on an access port, IV tubing, an extension set or a catheter. In some configurations, sensor 126 is disposed within a separate rigid attachment that includes a female luer port on one side and a male luer plug on the other and a sensor 126 disposed in the fluid path. This separate rigid attachment can be coupled to the IV fluid delivery system 150 at various locations. For example, in some instances sensor 126 is disposed near or within the catheter 152, such that the sensor 126 can test fluid just before it is infused into the patient. In other instances, sensor 126 is disposed near the source of the fluid, such as near container 122, so that the sensor 126 can test fluid and identify any error while there is time to stop infusion before the identified fluid enters the patient.

In some embodiments, identified information from sensor 126 of fluid identification station 140 is shown on a display device 134. For example, in instances where the administration is verified to be the same as the medication order by the prescribing physician, this information may be displayed on display device 134 and/or on the networked computer devices. In instances where an error in the administration is indicated, this error may also be displayed on display device 134.

In some embodiments, the fluid tracking system 442 of the present invention further comprises the ability to detect and identify safe or potentially hazardous drug-drug interactions. If dangerous drug mixtures are detected an alert and/or action can be initiated to prevent an administration from occurring. In some configurations, the fluid tracking system can further detect the flow rate of the IV fluid flowing through the IV fluid delivery system and can thus detect improper flow or line occlusions, which can initiate an alert.

In some configurations, IV fluid delivery system 150 is further configured to automatically stop IV fluid administration when it is determined that the identified contents and characteristics of the fluid, or the identified flow rate or other administration parameters do not match the prescribed order for the patient. For example, the IV fluid delivery system 150 may include one or more electronically controlled valves which are configured to stop fluid administration. Such an electronically controlled valve can be disposed within a smart pump 510, as shown and discussed in connection with FIG. 15, below.

With continued reference to FIG. 13, once the IV administration monitoring system 442 identifies contents and characteristics of the IV fluid, system 442 communicates this identified information to a computer network 146, or to a processor unit 132. This identified information may also be communicated to a computer system 472 at a nurse station, to a computer system 474 in a doctor's office, to a computer system 476 in a pharmacy (e.g., including both an on-site and an off-site pharmacy), and/or to other computer systems at other suitable locations. IV administration monitoring system 442 may further communicate various notifications, alerts, alarms, and other information.

Figure 14:
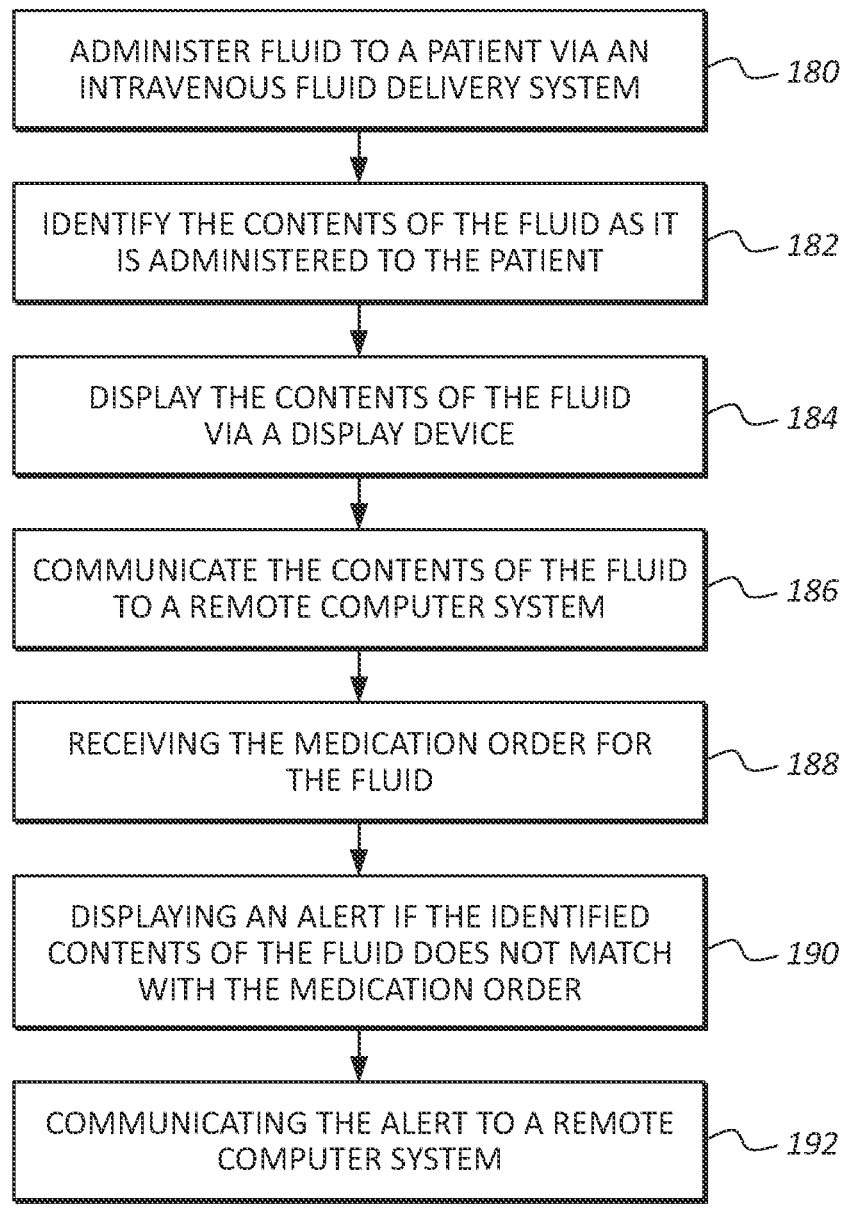
FIG. 14 is a flowchart illustrating a method for implementing an IV administration monitoring system in accordance with a representative embodiment of the present invention.

Referring now to FIG. 14, a flowchart of a method for using an IV administration monitoring system is provided. In some embodiments, the care provider initiates the administration of a fluid to a patient 180 using an intravenous fluid delivery system having fluid identifying capabilities in accordance with any of the various embodiments of the present invention. The care provider identifies the contents of the fluid using a fluid identification station of a fluid tracking system 182. In some embodiments, the care provider test fluid prior to administering the fluid to the patient. In other embodiments, the care provider administers a small fraction of the fluid to the patient, wait for a test of the fluid to be complete, verify the contents and characteristics of the fluid, and then proceeds to inject the remainder of the fluid.

Once identified, information related to the fluid is displayed on a display device of the fluid identification station 184. This information may also be communicated via a computer network or other computer system or devices 186, such as computer system at a nurse station, at a doctor's office, and/or at a pharmacy. Computer system can also include mobile computer system that may roam within an identified network.

In some embodiments, the fluid identification station communicates with a patient's EMR via an EMR software program or other computer executable program designed to receive data relating to the medication order of the fluid 188. Thus configured, the drug identity, and other contents and characteristics of the fluid can be matched against the medication order for the patient to verify the drug, the concentration, the route, the time of administration, and/or other such information.

In the event of an error, one or more actions or alerts can be initiated 190. For instance, an alert can be sent to one or more of the networked computer device which are configured to display the alert and/or initiate an audible alert 192. In some embodiments, the alert further comprises an identity and location of the patient, as well as the nature of the problem.

Figure 15:
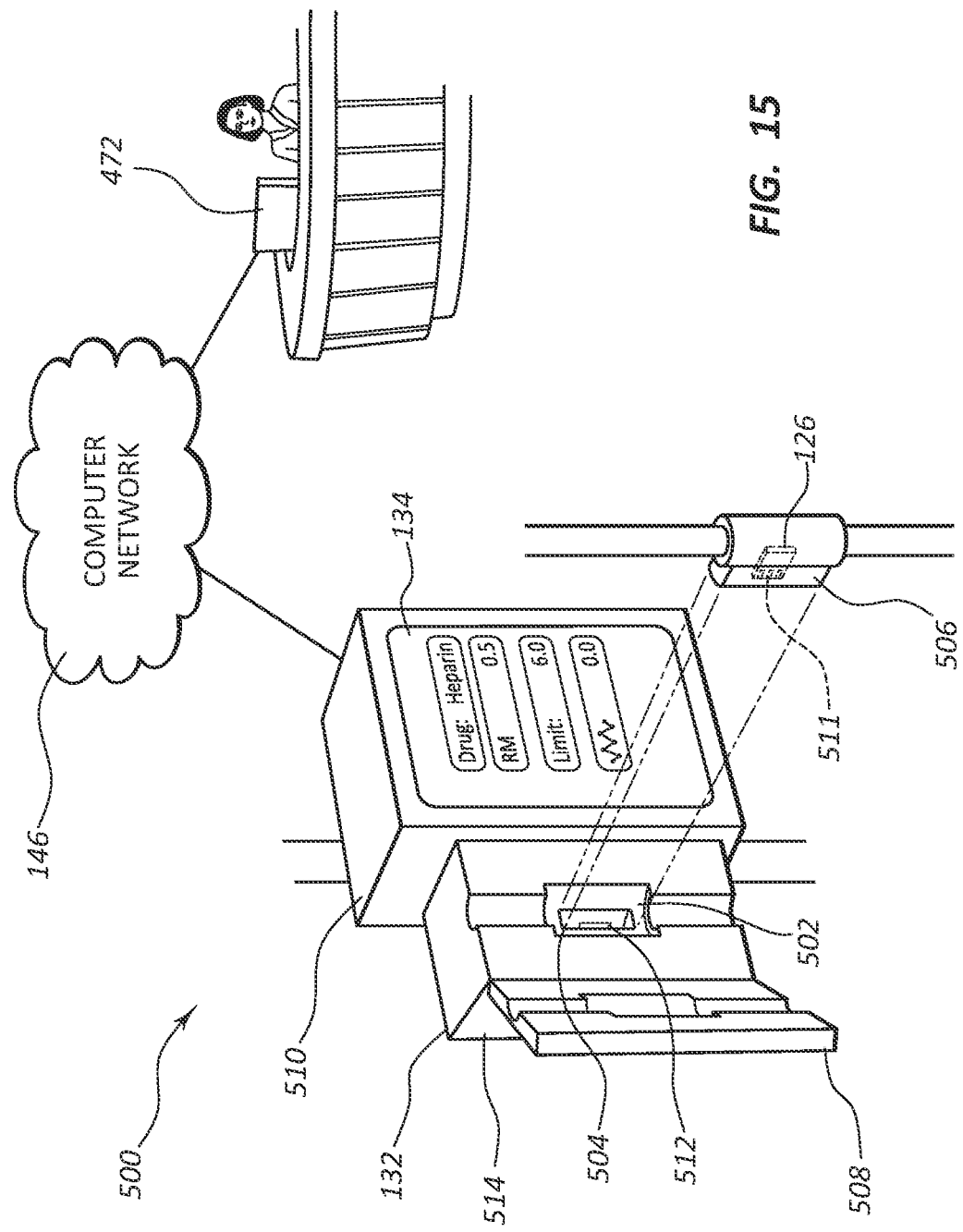
FIG. 15 is a diagrammatic view of an IV administration monitoring system comprising a fluid identification system having a sensor for detecting a fluid in accordance with a representative embodiment of the present invention.

Referring now to FIG. 15, a fluid identification station 500 is shown. In some embodiments, a fluid identification station 500 is provided which includes a smart pump 510. As mentioned above, a smart pump 510 may be programmed to include information regarding the contents of the fluid which is administered to the patient via the assistance of smart pump 510. For example, in some embodiments smart pump 510 is operably coupled to a processor unit 132 whereby smart pump 510 receives information from processor unit 132 regarding the identity and characteristics of a fluid. Accordingly, smart pump 510 is capable of automatically programming some or all pump parameters necessary to administer a fluid to a patient as ordered or prescribed by a care provider. In some configurations, smart pump 510 and processor unit 132 share a common housing and common display device 134. The combined smart pump 510 and processor unit 132 can also automatically limit or stop the flow of IV fluid to the patient when the processor unit 132 determines or detects and accuracy in the fluid or the administration parameters of the fluid for the patient.

As shown, the sensor 126 can be coupled to one or more contact surfaces 511 that electronically couple to one or more contact surfaces 512 of the processor unit 132. This electrical coupling may be secured to a housing 514 of the processor unit 132, wherein housing 514 receives and secures sensor housing 506, thereby surrounding the leads sensor 126. In some configurations, the housing 514 includes one or more external geometries 502, 504 that are shaped and sized to receive and secure sensor 126 within housing 514. Housing 514 may also include a door 508, latch, or other feature for selectively securing the sensor housing 506 within the housing 514.

Referring now to FIGS. 16-20, some embodiments of the present invention provide systems and methods for identifying, tracking and monitoring the disposal or wasting of a fluid. In hospitals and other care facilities, a physician, technician, or other medical personnel may be required to waste or discard a liquid containing following use of the liquid in treating a patient. Caution must be taken to prevent hazardous disposal, as well as misuse of the fluid, such as diverting the fluid for subsequent, unauthorized use.

Figure 16:
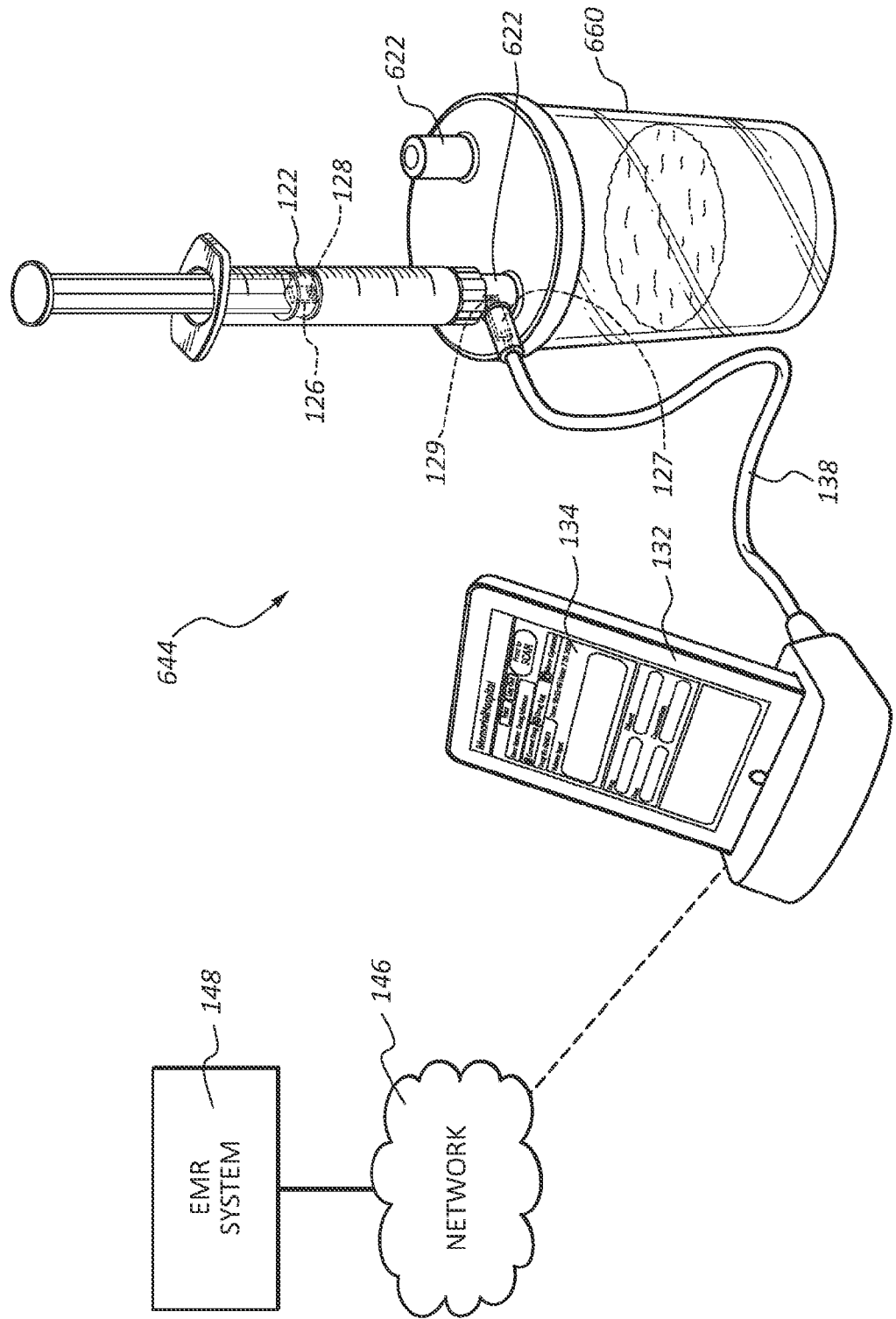
FIG. 16 is a perspective view of an IV fluid wasting system comprising a fluid identification system having a sensor for identifying a fluid in accordance with a representative embodiment of the present invention.
Figure 18:
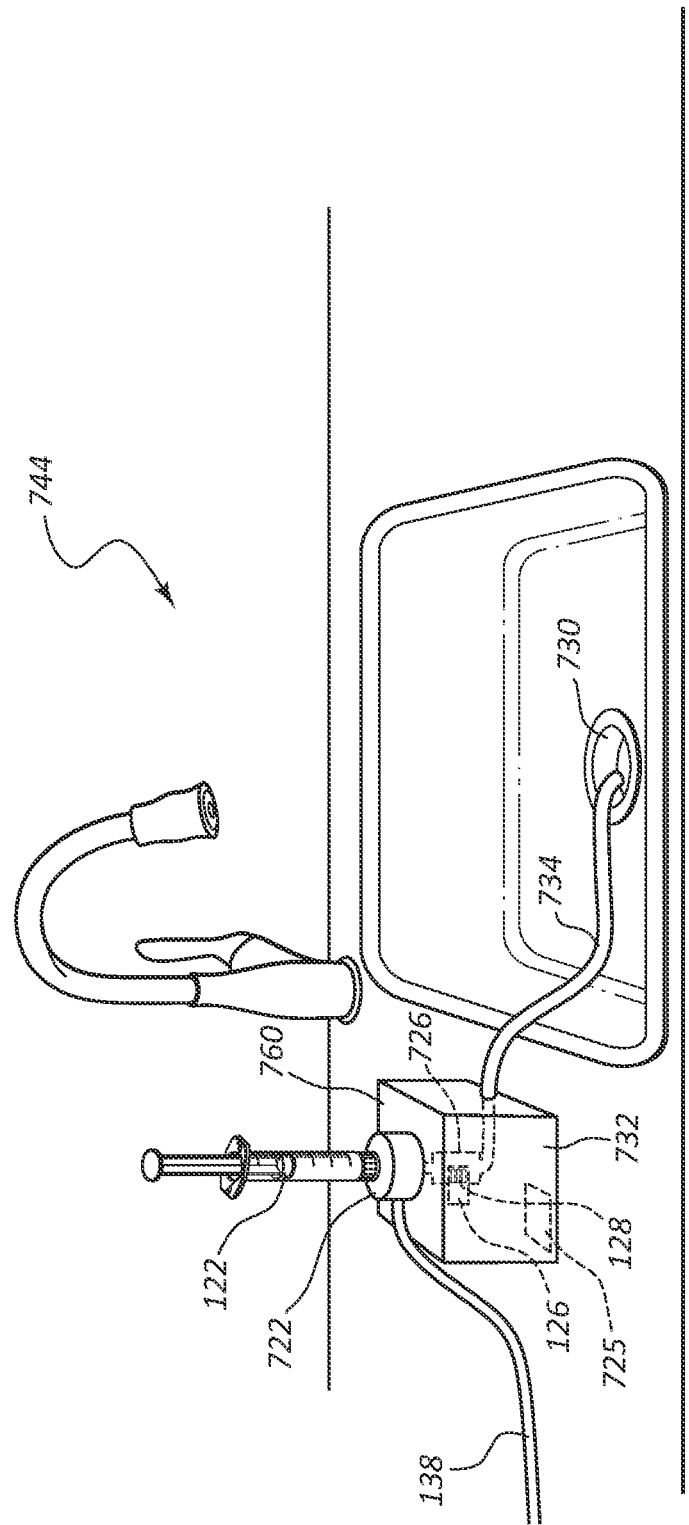
FIG. 18 is a perspective view of an IV fluid wasting system having a fluid identification system in accordance with a representative embodiment of the present invention.

With reference to FIG. 16, a fluid wasting system 644 is shown. System 644 generally comprises a disposal unit 660 having a lid 662 including one or more ports 622 for receiving a container 122 having a liquid for disposal. In some embodiments, a first port 622 is provided to receive a first type of container, and a second port 622 is provided to receive a second type of container. Disposal unit 660 further comprises a sensor 127 coupled to a portion of port 622 and in fluid communication with a fluid stored in container 122. In some embodiment, sensor 127 is positioned within port 622 so as to be in a fluid pathway 626 of port 622, as shown in FIG. 18. As such, fluid being wasted from container 122 into disposal unit 660 flows over sensor 127 thereby providing sensing measurements to processor unit 132.

Figure 17:
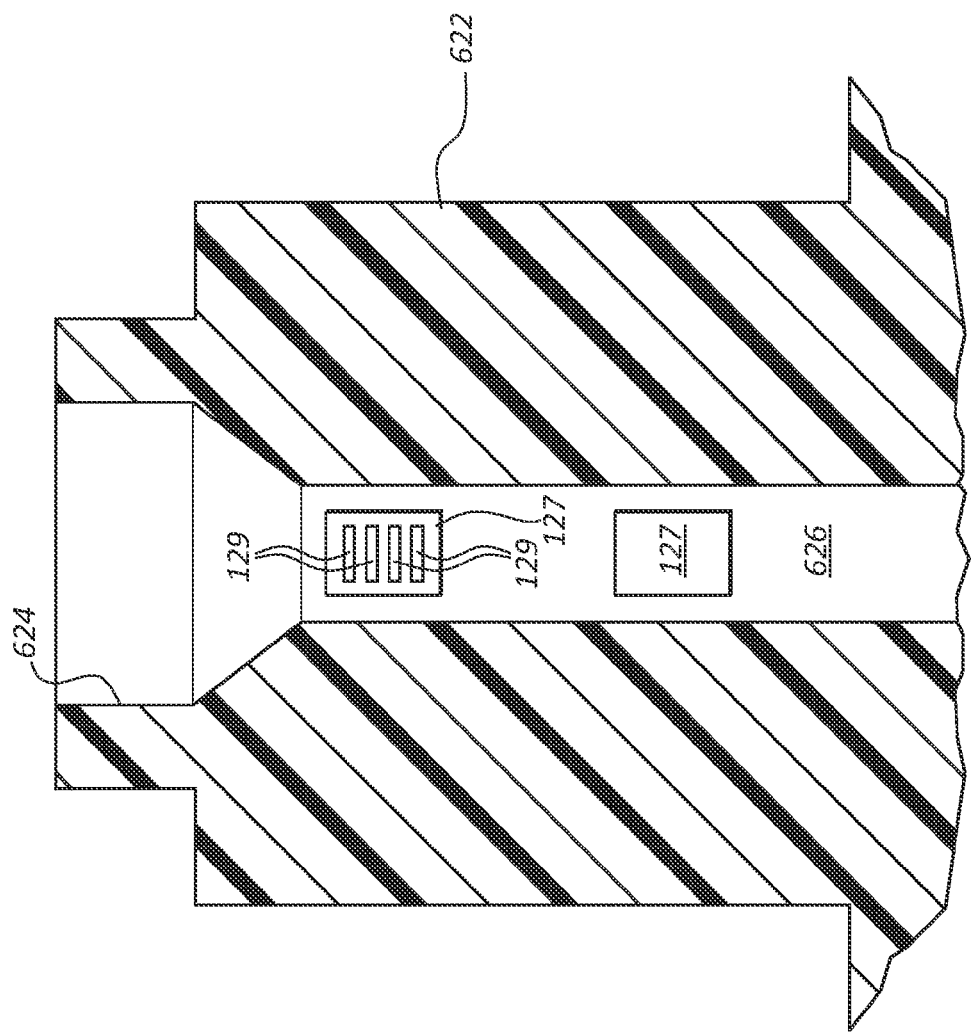
FIG. 17 is a cross section view of a port of a waste disposal unit having a plurality of sensors for identifying a fluid in accordance with a representative embodiment of the present invention.

With continued reference to FIGS. 16 and 17, in some embodiments port 662 further comprises a plurality of sensors 127 and sensor elements 129 positioned in fluid pathway 626, wherein each sensor element 129 is configured to detect at least one characteristic or identity of a fluid. Port 622 may further include an adapter 624 which is configured to compatibly receive a surface of container 122. Adapter 624 may include electrical contacts or other circuitry (not shown) whereby to establish communication between sensor 126 of container 122 and processor unit 132 via communication link 138. As such, processor unit 132 may collect, compare and verify fluid data from sensors 126 and 127 to determine proper and complete disposal.

In some instances, system 644 accesses information stored in the patient's EMR 148 to assist in determining whether a portion of the fluid may have been diverted, illegally modified, or stolen. For instance, in some embodiments the IV fluid wasting system 644 can verify whether the concentration of a constituent in the wasted fluid corresponds to what is recorded in the EMR 148.

As a non-limiting example, in one implementation an EMR 148 indicates that the container 122 originally included 10 mL of a fluid, 5 mL of which was prescribed and administered to a patient. Based on this information, IV fluid wasting system 644 determines that 5 mL of fluid will be wasted from container 122. If less than 5 mL of fluid is wasted, an error code is generated on processor unit 132 thereby alerting the user of the deficiency.

By way of further non-limiting example, in some embodiments EMR 148 contains data regarding the original or expected drug concentration of a wasted fluid. Therefore, in the event that the fluid has been diluted or otherwise tampered with, an error code is generated on processor unit 132 thereby alerting the user of the discrepancy.

Reference will now be made to FIG. 18, which illustrates another configuration of a waste disposal unit 760. Since some drugs are commonly wasted in a drain 730, a waste disposal unit 760 can lead fluids to a drain 730, while identifying the contents and characteristics of the fluid. As shown, in some configurations a waste disposal unit 760 includes a housing 732 having a port 722. As a fluid is introduced into the port 722, the fluid flows through a fluid path 726, which may include a tube 734 leading to drain 730. A sensor 126 can be disposed within the housing 732 with one or more sensing elements 128 disposed within the fluid path 726. The one or more sensing elements 128 can be in fluid communication with a fluid as it is wasted. In this way, the wasted fluid can be identified and recorded.

Various hospital or other care facilities and/or governmental regulations require that records be kept of some or all fluids that are wasted. Accordingly, when a fluid is wasted via waste disposal units 660 or 760, the fluid wasting system 644 or 744 can record one or more of the following pieces of information, including but not limited to the identity of any drugs within the fluid, the dose of any drugs, the concentration of any drugs, the identity of a diluent, the volume of the fluid wasted, the time and date of the wasting, patient information of the patient for whom the liquid was intended, the drug lot number, the drug maker, and the identity of the waster. This information can be recorded on a computer-readable media electrically coupled to the processor unit 132, including on an EMR 148, as discussed above.

Figure 19:
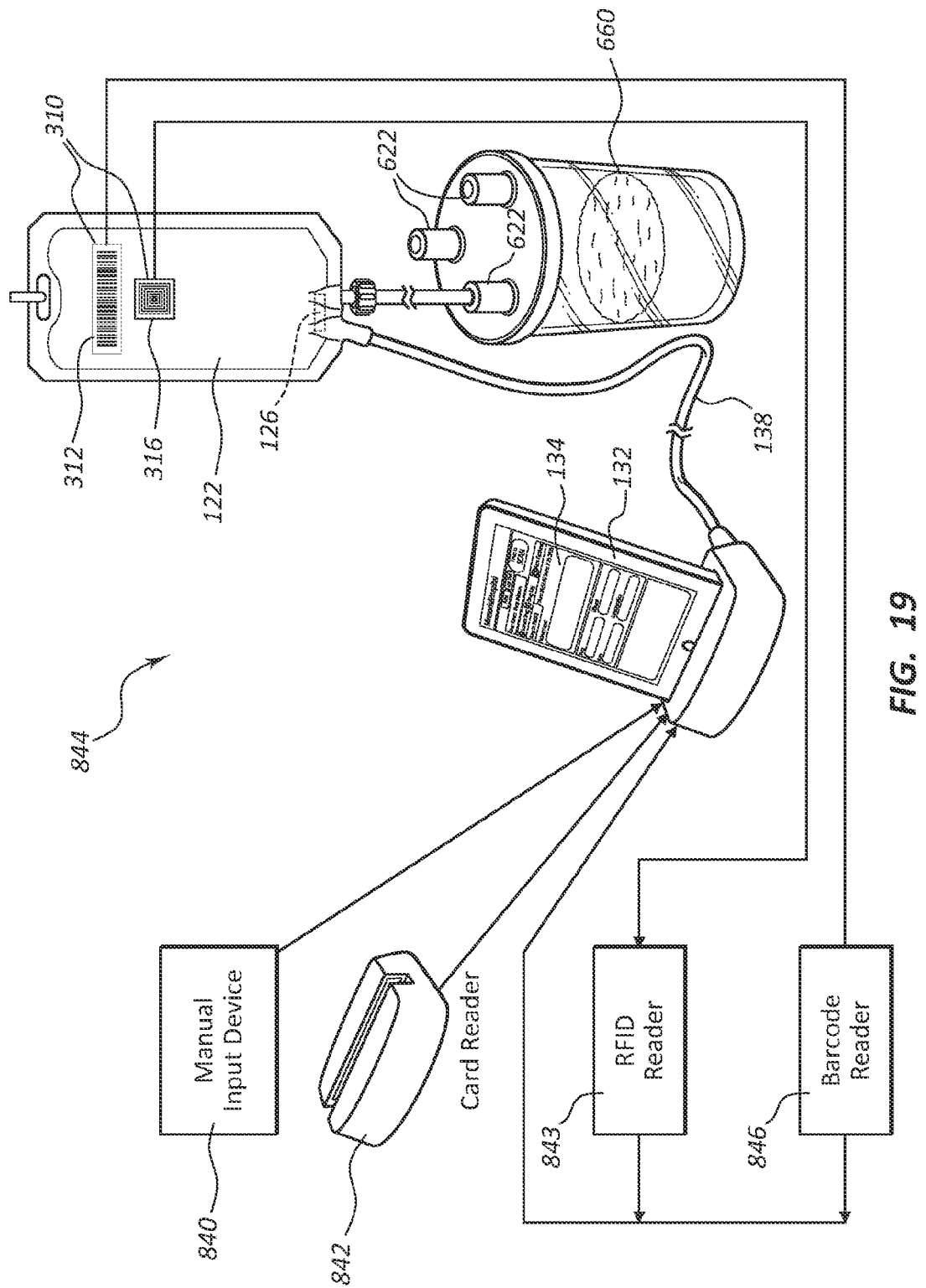
FIG. 19 is a diagrammatic view of an IV fluid wasting system operably coupled to a computer device and multiple input devices in accordance with a representative embodiment of the present invention.

Referring now to FIG. 19, a fluid wasting system 844 is shown. Fluid wasting system 744 includes various input devices coupled thereto configured to provide information to the processor unit 132. Through these and other input devices, processor unit 132 receives data relating to the identity of a fluid presently stored in container 122 and a previously-identified contents of the container 122. Processor unit 132 may further receive information regarding the identity of a patient for whom the fluid was prescribed or intended, the identity of the individual wasting the fluid, the original volume of the fluid placed in the container 122, the drug lot number, the drug maker, and other such information. In some embodiments, system 844 comprises a plurality of input devices, such as a manual input device 840 (i.e. a keypad, a mouse, or a touchpad electronically coupled to the processor unit 132 for manually entering information), a card reader 842, an RFID reader 843 and a barcode reader 846. Input devices of the present invention may be used to acquire additional information related to the individual wasting the fluid. For example, an input device may be used to acquire the identification of the person wasting the fluid.

Figure 20:
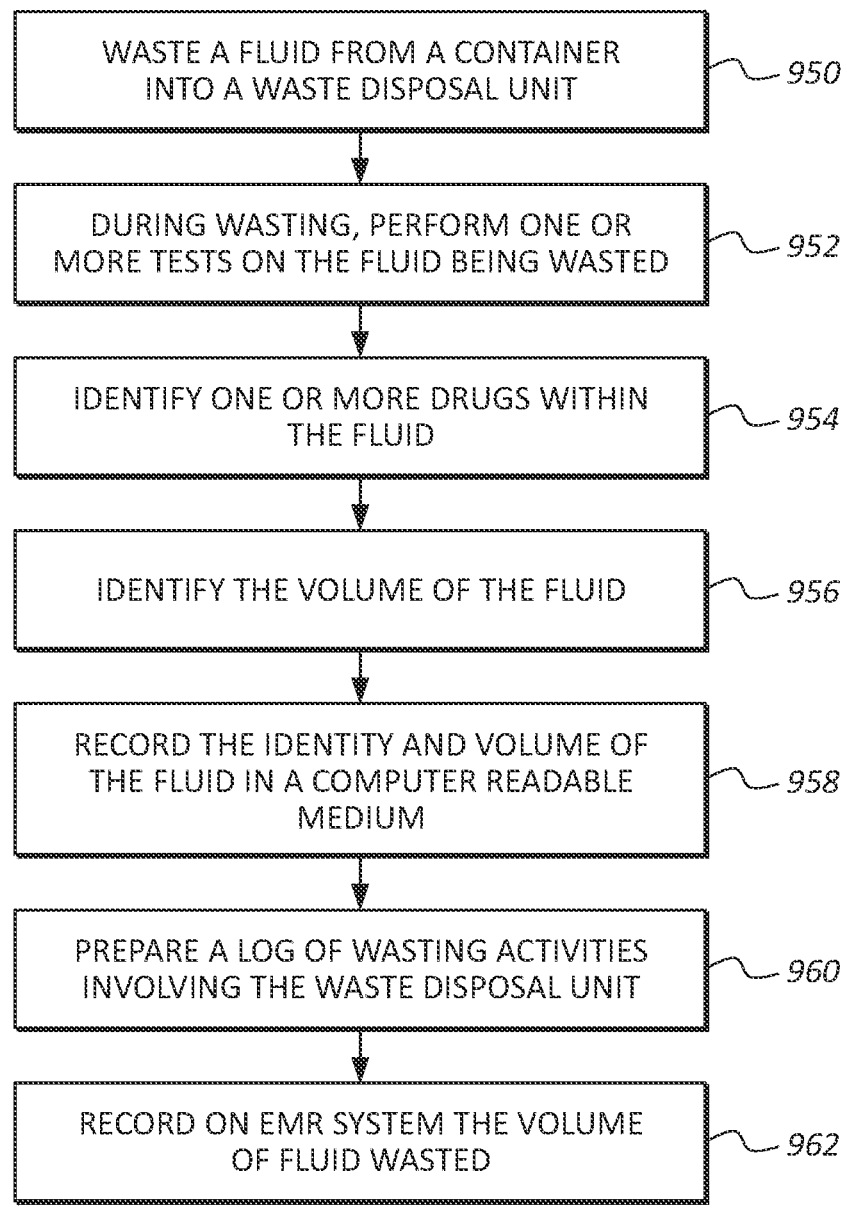
FIG. 20 is a flowchart illustrating a method for using an IV fluid wasting system in accordance with a representative embodiment of the present invention.

Reference will now be made to FIG. 20 which provides a flowchart of a method for monitoring the wasting of fluids. In some embodiments of the present invention, a method is provided having a first step 950 of wasting a fluid from a container into a waste disposal unit. As the fluid is being wasted, a sensor system performs one or more tests on the fluid being wasted into the waste disposal unit (at step 952). Using the sensing measurements, a processing unit of the system identifies one or more drugs within the fluid (at step 954). In addition to identifying the one or more drugs within the fluid, the sensor system identifies the volume of the wasted IV fluid (at step 956). After acquiring information about the container (i.e. the identity of the fluid, the contents of the fluid, the identity of the individual wasting the fluid, and/or other information), the fluid wasting system records this information in a computer readable medium (at step 958). In some embodiments, the fluid wasting system is configured to record this information in a log (or report) that records the information regarding the fluid wasting event (at step 960). In addition to preparing a log or report, the fluid wasting system may further record the amount of fluid wasted in the EMR of the patient for whom the IV fluid was prepared (at step 962).

Figure 21:
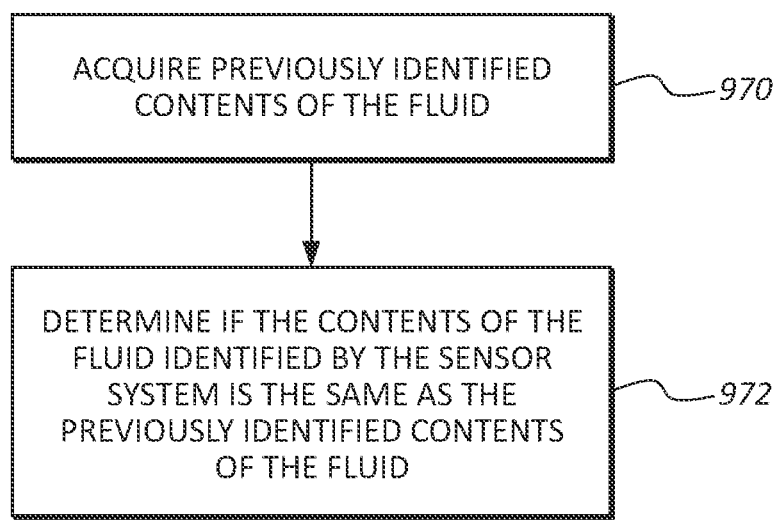
FIG. 21 is a flowchart illustrating a method for auditing the contents of a container comprising a fluid in accordance with a representative embodiment of the present invention.

With reference to FIG. 21, a method for auditing the contents of fluid wasted is shown. In some embodiments, a fluid wasting system accesses and acquires a previously determined identity of a fluid in a container (at step 970). The contents information can include the identity of one or more drugs within the fluid, the concentration of one or more drugs within the fluid, and/or the diluent of the fluid. After acquiring this information, a processor unit or other computer system compares the identity of the contents of the fluid being wasted with the previously determined identity of the fluid. The system then makes a determination as to whether there has been a change in the identity of the contents of the container (at step 972). If a difference is detected, the wasting system can flag the wasting event as potentially involving a drug diversion.

Figure 22:
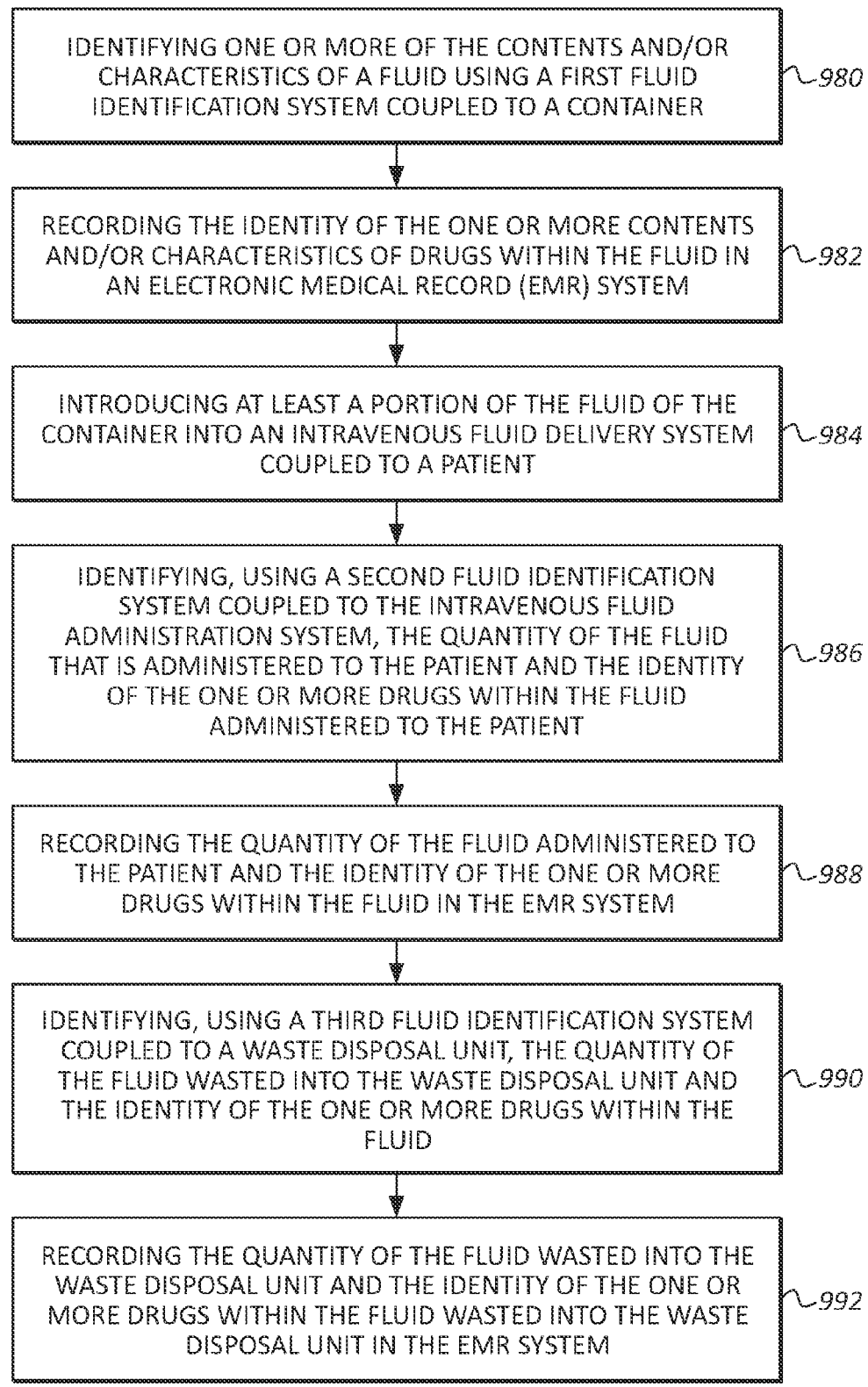
FIG. 22 is a flowchart illustrating a method for using multiple sensor systems to track a fluid in accordance with a representative embodiment of the present invention.

Referring now to FIG. 22, a method for monitoring the use of a fluid using one or more fluid identification stations is shown. In some embodiments of the present invention, a method is provided having a first step 980 whereby a user identifies one or more of the contents or characteristics of a fluid in a container using a first fluid identification station. The identity of the fluid or other identifying information for the fluid are then recorded in an electronic medical record (at step 982). Once recorded, this information can be used for inventory management, medical records, and patient billing. The identified contents and/or characteristics of the fluid can also be used to prepare a label for the container, which can even include a barcode or RFID chip that is electronically read. This early identification stage can verify proper compounding as well and provide identification to the container that will permit subsequent recipients of the container to verify it contents even if the subsequent recipient does not have a sensor system.

A second fluid identification station, such as an IV administration monitoring system, can be used to monitor the fluid while it is administered to a patient. Thus, in some embodiments at least a portion of the fluid from the container is introduced into the patient via an IV fluid delivery system coupled to the patient (at step 984). The second fluid identification station can identify the quantity of the fluid administered and the identity of one or more drugs within the fluid (at step 986). This information can then be recorded in the EMR system (at step 988). The second fluid identification station can also be configured to identify other contents or characteristics of the fluid not originally configured for detection by the first fluid identification station. The EMR system can correlate the information from the first and second fluid identification stations to verify that the patient is receiving the correct fluid, at the correct time, and with a correct administration procedure.

In some methods, a third fluid identification station, such as an IV fluid wasting system, is used to monitor the wasting of the fluid in the container (at step 990). In some instances, the entire volume of a fluid is administered to a patient. In other instances, a portion of a prescribed fluid remains unused. Depending on the nature of the prescribed fluid, this fluid may be reused or may need to be wasted. When wasted, a third fluid identification station is used to identify the fluid and thereby verify that a portion of the fluid has not been diverted. The third fluid identification station can also identify the volume of the fluid wasted. The third station may also be configured to identify one or more of the contents and/or characteristics of the fluid. This information may then be recorded in the ERM system and/or another such inventory or medical tracking system (at step 2992). Once recorded, the care facility can review, track, and/or monitor the lifecycle of the fluid by reviewing the various recorded events and measurements of the fluid as stored on the EMR system. The care facility can also keep automated or semi-automate records of the use of the fluid. These records can also be used to provide accurate billing records when a patient is billed only for the amount of fluid he or she received.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A system for monitoring a fluid, comprising:
a first fluid identification station having a first sensor for detecting a first characteristic of a fluid; and
a second fluid identification station having a second sensor for detecting a second characteristic of the fluid, wherein the first fluid identification station is operably connected to the second fluid identification station such that the second fluid identification station accesses and verifies the first characteristic of the fluid from the first fluid identification station, and the first fluid identification station accesses and verifies the second characteristic of the fluid from the second fluid identification station;
wherein the first fluid identification station comprises a first processing unit, and the second fluid identification station comprises a second processing unit, wherein the first and second processing units are operably connected via a computer network such that once the first fluid identification station identifies a characteristic of a fluid said first characteristic is stored on said computer network and such that once the second fluid identification station identifies a characteristic of a fluid said second characteristic is stored on said computer network such that proper fluid administration to a patient can be confirmed.

2. The system of claim 1, further comprising a third fluid identification station having a third sensor for detecting a third characteristic of the fluid, wherein the third fluid identification station is operably connected to the first and second fluid identification stations such that the first and second fluid identification stations accesses the third characteristic of the fluid from the third fluid identification station, and the third fluid identification station accesses the first and second characteristics of the fluid from the first and second fluid identification stations, respectively.

3. The system of claim 2, wherein at least one of the first, second, and third characteristics of the fluid is selected from the group consisting of: a diluent of the fluid, a concentration of a constituent within the fluid, an identity of a constituent within the fluid, a temperature of the fluid, a concentration of the fluid, an age of the fluid, an expiration date of the fluid, and a dosage of the fluid.

4. The system of claim 1, further comprising a computer network wherein the first and second fluid identification stations are operably connected via the computer network.

5. The system of claim 4, further comprising an electronic medical record operably connected to at least one of the first fluid identification station and the second fluid identification station via the computer network.

6. The system of claim 1, further comprising a processing unit operably connected to at least one of the first sensor and the second sensor, wherein the processing unit receives a sensing measurement from the connected sensors.

7. The system of claim 6, wherein the processing unit comprises a computer device.

8. The system of claim 1, wherein the first and second sensors further comprise a sensing element configured to detect at least one characteristic of the fluid, the sensing element being positioned so as to be in contact with the fluid.

9. The system of claim 8, wherein the sensing element comprises a plurality of sensing elements.

10. The system of claim 1, further comprising an output device coupled to the first fluid identification station and configured to prepare a computer recognizable code with data communicating the first characteristic of the fluid.

11. The system of claim 10, wherein the output device is at least one of a printer and an RFID programmer.

12. The system of claim 10, further comprising an input device coupled to the first fluid identification station and configured to read the computer recognizable code.

13. The system of claim 1, further comprising a display device for communicating the first and second characteristics of the fluid to a user.

14. The system of claim 2, further comprising a plurality of fluid identification stations.

15. The system of claim 14, wherein the plurality of fluid identification stations are operably connected via the computer network.

16. A method of monitoring the use of a fluid, comprising:
identifying a first use of a fluid using a first fluid identification station having a first sensor for detecting a first characteristic of the fluid; and
identifying a second use of the fluid using a second fluid identification station having a second sensor for detecting a second characteristic of the fluid, wherein the first fluid identification station is operably connected to the second fluid identification station such that the second fluid identification station accesses and verify the first characteristic of the fluid from the first fluid identification station, and the first fluid identification station accesses and verify the second characteristic of the fluid from the second fluid identification station;
wherein the first fluid identification station comprises a first processing unit, and the second fluid identification station comprises a second processing unit, wherein the first and second processing units are operably connected via a computer network such that once the first fluid identification station identifies a characteristic of a fluid said first characteristic is stored on said computer network and such that once the second fluid identification station identifies a characteristic of a fluid said second characteristic is stored on said computer network such that proper fluid administration to a patient can be confirmed.

17. The method of claim 14 further comprising a step for recording the first and second characteristics of the fluid in an electronic medical record.

18. The method of claim 14, wherein at least one of the first and second characteristics of the fluid is selected from the group consisting of: a diluent of the fluid, a concentration of a constituent within the fluid, an identity of a constituent within the fluid, a temperature of the fluid, a concentration of the fluid, an age of the fluid, an expiration date of the fluid, and a dosage of the fluid.

* * * * *